US008664399B2

(12) United States Patent
Abelman et al.

(10) Patent No.: US 8,664,399 B2
(45) Date of Patent: Mar. 4, 2014

(54) SUBSTITUTED HETEROCYCLIC COMPOUNDS AS ION CHANNEL MODULATORS

(71) Applicant: Gilead Sciences, Inc., Foster City, CA (US)

(72) Inventors: Matthew Abelman, Mill Valley, CA (US); Robert H. Jiang, Cupertino, CA (US); Jeff Zablocki, Los Altos, CA (US)

(73) Assignee: Gilead Sciences, Inc., Foster City, CA (US)

(*) Notice: Subject to any disclaimer, the term of this patent is extended or adjusted under 35 U.S.C. 154(b) by 0 days.

(21) Appl. No.: 13/706,879

(22) Filed: Dec. 6, 2012

(65) Prior Publication Data

US 2013/0102632 A1 Apr. 25, 2013

Related U.S. Application Data

(63) Continuation of application No. 12/617,513, filed on Nov. 12, 2009, now abandoned.

(60) Provisional application No. 61/114,952, filed on Nov. 14, 2008.

(51) Int. Cl.
*C07D 413/04* (2006.01)
*C07D 215/54* (2006.01)
*C07D 215/14* (2006.01)
*C07D 401/06* (2006.01)

(52) U.S. Cl.
USPC ........... 546/159; 546/167; 546/168; 546/170; 546/173

(58) Field of Classification Search
None
See application file for complete search history.

(56) References Cited

FOREIGN PATENT DOCUMENTS

| WO | WO-9308174 A1 | 4/1993 |
|---|---|---|
| WO | WO-0244157 A2 | 6/2002 |
| WO | WO-02096873 A1 | 12/2002 |
| WO | WO-03-066055 A1 | 8/2003 |
| WO | WO-2008144483 A2 | 11/2008 |

OTHER PUBLICATIONS

Paesha et al., LiBr-catalyzed simple and efficient synthesis of some novel substituted quinolines via Friedlander heteroannulation reaction, 37(24) Synthetic Communc's 4319-4326 (2007) (CAS Abstract).*
Atechian, S. et al. (2007) "New vistas in quinoline synethesis", *Tetrahedron*, vol. 63, pp. 2811-2823.
International Search Report for PCT/US2009/064208, International Filing Date Nov. 12, 2009, mailed Feb. 18, 2010.
Kempter, G. et al., (1996), "Heterocyclics From Amino Ketones. XI. Singlestage Synthesis of Substituted 1, 2-dihydroacridines" *Journal Fuer Praktische Chrmie (Leipzig)*, vol. 34(5-6), pp. 298-311.
Mikata, Y. et al. (2001) "NAD/NADH Models with Axial/Central Chiralities: Superiority of the Quinoline Ring System" *Journal of Organic Chemistry* vol. 66(5), pp. 1590-1599.
Office Action for Thailand Application No. 0901005092 mailed Apr. 7, 2011.
Rautio, J. et al., (2008), "Prodrugs: Design and Clinical Applications", *Nature Reviews/Drug Discovery*, vol. 7, p. 255.
Selvam, N.P. et al. (2006) "Water Mediated Synthesis of Substituted Quinolines—A New Green Approach to the Friedlander Annulation", *J. Heterocyclic Chem.* vol. 43, pp. 1379-1382.
Toi et al. (1969) "o-Aminobenzophenone derivatives. III. Syntheses of 2,3,4,6-tetrasubstituted and 2,4,6-trisubstituted quinoline derivatives", *Nippon Kagaku Zasshi*, vol. 90, pp. 81-85.
Vippagunta, S. et al. (2001), "Crystalline Solids" *Advanced Drug Delivery Reviews*, vol. 48, pp. 3-26.

* cited by examiner

*Primary Examiner* — Janet L Andres
*Assistant Examiner* — Timothy R Rozof
(74) *Attorney, Agent, or Firm* — Francis O. Ginah; J. Elin Hartrum

(57) ABSTRACT

The present invention relates to sodium channel inhibitors of Formula (I):

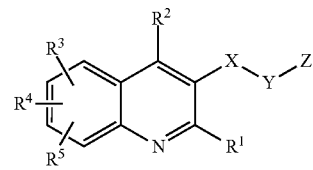

in which $R^1$, $R^2$, $R^3$, $R^4$, $R^5$, X, Y, and Z are as defined herein, and to their use in the treatment of various disease states, including cardiovascular diseases and diabetes.
The invention also relates to methods for the preparation of the compounds, and to pharmaceutical compositions containing such compounds.

2 Claims, No Drawings

SUBSTITUTED HETEROCYCLIC COMPOUNDS AS ION CHANNEL MODULATORS

CROSS-REFERENCE TO RELATED APPLICATIONS

This application is a Continuation of U.S. patent application Ser. No. 12/617,513, filed Nov. 12, 2009, which claims priority to U.S. Provisional Patent Application Ser. No. 61/114,952, filed Nov. 14, 2008, the entire disclosure of which is hereby incorporated by reference.

FIELD OF THE INVENTION

The present invention relates to novel compounds and to their use in the treatment of various disease states, including cardiovascular diseases and diabetes. The invention also relates to methods for their preparation, and to pharmaceutical compositions containing such compounds.

BACKGROUND

The late sodium current ($I_{NaL}$) is a sustained component of the fast Na$^+$ current of cardiac myocytes and neurons. Many common neurological and cardiac conditions are associated with abnormal ($I_{NaL}$) enhancement, which contributes to the pathogenesis of both electrical and contactile dysfunction in mammals. See, for example, Pathophysiology and Pharmacology of the Cardiac "Late Sodium Current", Pharmacology and Therapeutics 119 (2008) 326-339. Accordingly, pharmaceutical compounds that selectively inhibit ($I_{NaL}$) in mammals are useful in treating such disease states.

One example of a selective inhibitor of ($I_{NaL}$) is RANEXA®, a compound approved by the FDA for the treatment of chronic stable angina pectoris. RANEXA® has also been shown to be useful for the treatment of a variety of cardiovascular diseases, including ischemia, reperfusion injury, arrhythmia and unstable angina, and also for the treatment of diabetes. It would be desirable to provide novel compounds that selectively inhibit ($I_{NaL}$) in mammals, and that have a similar spectrum of activity as RANEXA®, but with a lower potential for blocking the potassium hERG channel.

SUMMARY OF THE INVENTION

Accordingly, the present invention provides novel compounds of Formula (I) that function as late sodium channel blockers:

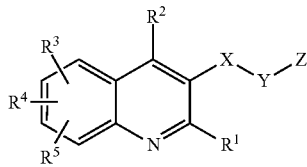

Formula (I)

wherein:
R$^1$ is amino or alkyl of 1-6 carbon atoms optionally substituted by halo, alkoxy of 1-6 carbon atoms, or phenoxy optionally substituted by 1, 2, or 3 substituents independently chosen from halo, alkyl of 1-6 carbon atoms, and alkoxy of 1-6 carbon atoms; or R$^1$ is alkyl of 1-6 carbon atoms substituted by —NR$^6$R$^7$, in which R$^6$ and R$^7$ are independently chosen from hydrogen or alkyl of 1-6 carbon atoms, or R$^6$ and R$^7$ when combined with the nitrogen atom to which they are attached is a nitrogen-bearing heterocyclyl or heteroaryl group;

R$^2$ is alkyl of 1-6 carbon atoms, phenyl, or heteroaryl, all of which are optionally substituted by halo, alkyl of 1-6 carbon atoms, hydroxyl, cyano, alkoxy of 1-6 carbon atoms, or —C(O)R, in which R is alkoxy of 1-6 carbon atoms or —NR$^6$R$^7$, in which R$^6$ and R$^7$ are independently chosen from hydrogen or alkyl of 1-6 carbon atoms;

R$^3$, R$^4$, and R$^5$ are independently chosen from hydrogen, halo, alkyl of 1-6 carbon atoms, hydroxyl, cyano, or alkoxy of 1-6 carbon atoms;

X is a covalent bond, cyano, —C(O)—, —C(O)O—, —CH(OH)—, or —C(O)NR$^6$R$^7$;

Y is a covalent bond, alkylene of 1-6 carbon atoms, or heteroaryl;

Z is a covalent bond, hydrogen, phenyl, benzyl, or cycloalkyl of 3-8 carbon atoms, all of which are optionally substituted by phenyl or heteroaryl, both of which are optionally substituted by 1, 2, or 3 substituents independently chosen from halo, alkyl of 1-6 carbon atoms, alkoxy of 1-6 carbon atoms, and —C(O)R$^8$, where R$^8$ is alkyl of 1-6 carbon atoms, alkoxy of 1-6 carbon atoms, or —NR$^6$R$^7$, in which R$^6$ and R$^7$ are independently chosen from hydrogen or alkyl of 1-6 carbon atoms; or Z is phenyl optionally substituted by 1, 2, or 3 substituents independently chosen from halo, alkyl of 1-6 carbon atoms optionally substituted by heteroaryl, and alkoxy of 1-6 carbon atoms;

with the proviso that X, Y and Z cannot all be covalent bonds; and the pharmaceutically acceptable salts, esters, prodrugs, or solvates thereof.

In one embodiment the invention provides pharmaceutical formulations comprising a therapeutically effective amount of a compound of Formula (I) and at least one pharmaceutically acceptable excipient.

In another embodiment the invention provides a method of using the compounds of Formula (I) in the treatment of a disease or condition in a mammal that is amenable to treatment by a late sodium channel blocker. Accordingly, the compounds of the invention and their therapeutically acceptable salts, esters, tautomeric forms are of use as medicaments for the treatment of, for example, cardiovascular diseases such as atrial and ventricular arrhythmias, heart failure (including congestive heart failure, diastolic heart failure, systolic heart failure, acute heart failure), Prinzmetal's (variant) angina, stable and unstable angina, exercise induced angina, congestive heart disease, ischemia, recurrent ischemia, reperfusion injury, myocardial infarction, acute coronary syndrome, peripheral arterial disease, and intermittent claudication. Such diseases include diabetes, and conditions related to diabetes, e.g. diabetic peripheral neuropathy.

Such diseases also include conditions affecting the neuromuscular system resulting in pain, seizures, or paralysis. Also included are central nervous system disorders such as acute, chronic, neuropathic, or inflammatory pain, migraine, cluster headaches, trigeminal neuralgia, herpetic neuralgia, general neuralgias, epilepsy or epilepsy conditions, and neurodegenerative disorders.

DETAILED DESCRIPTION

As used in the present specification, the following words and phrases are generally intended to have the meanings as set forth below, except to the extent that the context in which they are used indicates otherwise.

The term "alkyl" refers to a monoradical branched or unbranched saturated hydrocarbon chain having from 1 to 20 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to:
1) an alkyl group as defined above, having 1, 2, 3, 4 or 5 substituents, (typically 1, 2, or 3 substituents) selected from the group consisting of alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or
2) an alkyl group as defined above that is interrupted by 1-10 atoms (e.g. 1, 2, 3, 4, or 5 atoms) independently chosen from oxygen, sulfur and NRa-, where Ra is chosen from hydrogen, alkyl, cycloalkyl, alkenyl, cycloalkenyl, alkynyl, aryl, heteroaryl and heterocyclyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2; or
3) an alkyl group as defined above that has both 1, 2, 3, 4 or 5 substituents as defined above and is also interrupted by 1-10 atoms (e.g. 1, 2, 3, 4, or 5 atoms) as defined above.

The term "lower alkyl" refers to a monoradical branched or unbranched saturated hydrocarbon chain having 1, 2, 3, 4, 5, or 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents (typically 1, 2, or 3 substituents), as defined for substituted alkyl, or a lower alkyl group as defined above that is interrupted by 1, 2, 3, 4, or 5 atoms as defined for substituted alkyl, or a lower alkyl group as defined above that has both 1, 2, 3, 4 or 5 substituents as defined above and is also interrupted by 1, 2, 3, 4, or 5 atoms as defined above.

The term "alkylene" refers to a diradical of a branched or unbranched saturated hydrocarbon chain, typically having from 1 to 20 carbon atoms (e.g. 1-10 carbon atoms, or 1, 2, 3, 4, 5 or 6 carbon atoms). This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—), and the like.

The term "lower alkylene" refers to a diradical of a branched or unbranched saturated hydrocarbon chain, typically having 1, 2, 3, 4, 5, or 6 carbon atoms.

The term "substituted alkylene" refers to:
(1) an alkylene group as defined above having 1, 2, 3, 4, or 5 substituents (typically 1, 2, or 3 substituents) selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or
(2) an alkylene group as defined above that is interrupted by 1-10 groups (e.g. 1, 2, 3, 4, or 5 groups) independently chosen from —O—, —S—, sulfonyl, —C(O)—, —C(O)O—, —C(O)N—, and —NRa-, where Ra is chosen from hydrogen, optionally substituted alkyl, cycloalkyl, cycloalkenyl, aryl, heteroaryl and heterocyclyl; or
(3) an alkylene group as defined above that has both 1, 2, 3, 4 or 5 substituents as defined above and is also interrupted by 1-10 groups as defined above. Examples of substituted alkylenes are chloromethylene (—CH(Cl)—), aminoethylene (—CH(NH$_2$)CH$_2$—), methylaminoethylene (—CH(NHMe)CH$_2$—), 2-carboxypropylene isomers (—CH$_2$CH(CO$_2$H)CH$_2$—), ethoxyethyl (—CH$_2$CH$_2$O—CH$_2$CH$_2$—), ethylmethylaminoethyl (—CH$_2$CH$_2$—N(CH$_3$)—CH$_2$CH$_2$—), 1-ethoxy-2-(2-ethoxy-ethoxy)ethane (—CH$_2$CH$_2$O—CH$_2$CH$_2$—OCH$_2$CH$_2$—OCH$_2$CH$_2$—), and the like.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "alkoxy" refers to the group R—O—, where R is optionally substituted alkyl or optionally substituted cycloalkyl, or R is a group —Y—Z, in which Y is optionally substituted alkylene and Z is optionally substituted alkenyl, optionally substituted alkynyl; or optionally substituted cycloalkenyl, where alkyl, alkenyl, alkynyl, cycloalkyl and cycloalkenyl are as defined herein. Typical alkoxy groups are alkyl-O— and include, by way of example, methoxy, ethoxy, n-propoxy, iso-propoxy, n-butoxy, tert-butoxy, sec-butoxy, n-pentoxy, n-hexyloxy, 1,2-dimethylbutoxy, and the like.

The term "lower alkoxy" refers to the group R—O— in which R is optionally substituted lower alkyl as defined above. This term is exemplified by groups such as methoxy, ethoxy, n-propoxy, iso-propoxy, n-butoxy, iso-butoxy, t-butoxy, n-hexyloxy, and the like.

The term "alkylthio" refers to the group R—S—, where R is as defined for alkoxy.

The term "alkenyl" refers to a monoradical of a branched or unbranched unsaturated hydrocarbon group typically having from 2 to 20 carbon atoms (more typically from 2 to 10 carbon atoms, e.g. 2 to 6 carbon atoms) and having from 1 to 6 carbon-carbon double bonds, e.g. 1, 2, or 3 carbon-carbon double bonds. Typical alkenyl groups include ethenyl (or vinyl, i.e. —CH═CH$_2$), 1-propylene (or allyl, —CH$_2$CH═CH$_2$), isopropylene (—C(CH$_3$)═CH$_2$), bicyclo [2.2.1]heptene, and the like. In the event that alkenyl is attached to nitrogen, the double bond cannot be alpha to the nitrogen.

The term "lower alkenyl" refers to alkenyl as defined above having from 2 to 6 carbon atoms.

The term "substituted alkenyl" refers to an alkenyl group as defined above having 1, 2, 3, 4 or 5 substituents (typically 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "alkynyl" refers to a monoradical of an unsaturated hydrocarbon, typically having from 2 to 20 carbon atoms (more typically from 2 to 10 carbon atoms, e.g. 2 to 6 carbon atoms) and having from 1 to 6 carbon-carbon triple bonds e.g. 1, 2, or 3 carbon-carbon triple bonds. Typical alkynyl groups include ethynyl (—C≡CH), propargyl (or propynyl, —C≡CCH3), and the like. In the event that alkynyl is attached to nitrogen, the triple bond cannot be alpha to the nitrogen.

The term "substituted alkynyl" refers to an alkynyl group as defined above having 1, 2, 3, 4 or 5 substituents (typically 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aminocarbonyl" refers to the group —C(O)NRR where each R is independently hydrogen, alkyl, cycloalkyl, aryl, heteroaryl, heterocyclyl or where both R groups are joined to form a heterocyclic group (e.g., morpholino). Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "ester" or "carboxyester" refers to the group —C(O)OR, where R is alkyl, cycloalkyl, aryl, heteroaryl, or heterocyclyl, which may be optionally further substituted by alkyl, alkoxy, halogen, CF$_3$, amino, substituted amino, cyano, or —S(O)$_n$Ra, in which Ra is alkyl, aryl, or heteroaryl and n is 0, 1 or 2.

The term "acylamino" refers to the group —NRC(O)R where each R is independently hydrogen, alkyl, aryl, heteroaryl, or heterocyclyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "acyloxy" refers to the groups —OC(O)-alkyl, —OC(O)-cycloalkyl, —OC(O)-aryl, —OC(O)-heteroaryl, and —OC(O)-heterocyclyl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl, fluorenyl, and anthryl). Typical aryls include phenyl, fluorenyl, naphthyl, anthryl, and the like. Note that an aryl group may be attached to the rest of a molecule via one or more than one (e.g. two) site(s), as in the case of certain compounds of Formula (I) as described elsewhere herein. Similarly, a heteroaryl group or a heterocyclyl group may be attached to the rest of a molecule via one or more than one (e.g. two) site, as in the case of certain compounds of Formula (I), as described elsewhere herein. For example a heteroaryl group or a heterocyclyl group may bind to two separate portions of molecule, e.g. may be a linker moiety joining the two separate portions of the molecule, e.g. a compound of Formula (I).

Unless otherwise constrained by the definition for the aryl substituent, such aryl groups can optionally be substituted with 1, 2, 3, 4 or 5 substituents (typically 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano and —S(O)$_n$R, where R is alkyl, aryl, or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "amino" refers to the group —NH$_2$.

The term "substituted amino" refers to the group —NRR where each R is independently selected from the group consisting of hydrogen, alkyl, cycloalkyl, aryl, heteroaryl and heterocyclyl provided that both R groups are not hydrogen, or a group —Y—Z, in which Y is optionally substituted alkylene and Z is alkenyl, cycloalkenyl, or alkynyl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "carboxyalkyl" refers to the groups —C(O)O-alkyl, —C(O)O-cycloalkyl, where alkyl and cycloalkyl are as defined herein, and may be optionally further substituted by alkyl, alkenyl, alkynyl, alkoxy, halogen, CF$_3$, amino, substituted amino, cyano, or —S(O)$_n$R, in which R is alkyl, aryl, or heteroaryl and n is 0, 1 or 2.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and bicyclo[2.2.1]heptane, or cyclic alkyl groups to which is fused an aryl group, for example indan, and the like.

The term "substituted cycloalkyl" refers to cycloalkyl groups having 1, 2, 3, 4 or 5 substituents (typically 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. The term "substituted cycloalkyl" also includes cycloalkyl groups wherein one or more of the annular carbon atoms of the cycloalkyl group is a carbonyl group (i.e. an oxygen atom is oxo to the ring). Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "halogen" or "halo" refers to fluoro, bromo, chloro, and iodo.

The term "acyl" denotes a group —C(O)R, in which R is hydrogen, optionally substituted alkyl, optionally substituted cycloalkyl, optionally substituted heterocyclyl, optionally substituted aryl, and optionally substituted heteroaryl.

The term "heteroaryl" refers to a group comprising 1 to 15 carbon atoms and 1 to 4 heteroatoms selected from oxygen, nitrogen, and sulfur within at least one ring. The term "heteroaryl" is generic to the terms "aromatic heteroaryl" and "partially saturated heteroaryl". The term "aromatic heteroaryl" refers to a heteroaryl in which at least one ring is aromatic. Examples of aromatic heteroaryls include pyrrole, thiophene, pyridine, quinoline, pteridine, oxadiazole, and the like. The term "partially saturated heteroaryl" refers to a heteroaryl having a structure equivalent to an underlying aromatic heteroaryl which has had one or more double bonds in an aromatic ring of the underlying aromatic heteroaryl saturated. Examples of partially saturated heteroaryls include dihydropyrrole, dihydropyridine, 1,2,3,4-tetrahydronaphthalene.

Unless otherwise constrained by the definition for the heteroaryl substituent, such heteroaryl groups can be optionally substituted with 1 to 5 substituents (typically 1, 2, or 3 substituents) selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl (an alkyl ester), arylthio, heteroaryl, heteroarylthio, heterocyclylthio, thiol, alkylthio, aryl, aryloxy, aralkyl, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2. Such heteroaryl groups can have a single ring (e.g., pyridyl or furyl) or multiple condensed rings (e.g., indolizinyl, benzothiazole, or benzothienyl). Examples of nitrogen heterocyclyls and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxy-nitrogen containing heteroaryl compounds.

The term "heteroaryloxy" refers to the group heteroaryl-O—.

The term "heterocyclyl" refers to a monoradical saturated group having a single ring or multiple condensed rings, having from 1 to 40 carbon atoms and from 1 to 10 hetero atoms, preferably 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5 substituents (typically 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2. Heterocyclic groups can have a single ring or multiple condensed rings. Preferred heterocyclics include tetrahydrofuranyl, morpholino, piperidinyl, and the like.

The term "thiol" refers to the group —SH.

The term "substituted alkylthio" refers to the group —S-substituted alkyl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, aryl, or heteroaryl. "Substituted sulfoxide" refers to a group —S(O)R, in which R is substituted alkyl, substituted aryl, or substituted heteroaryl, as defined herein.

The term "sulfone" refers to a group —S(O)$_2$R, in which R is alkyl, aryl, or heteroaryl. "Substituted sulfone" refers to a group —S(O)$_2$R, in which R is substituted alkyl, substituted aryl, or substituted heteroaryl, as defined herein.

The term "keto" refers to a group —C(O)—. The term "thiocarbonyl" refers to a group —C(S)—. The term "carboxy" refers to a group —C(O)—OH.

"Optional" or "optionally" means that the subsequently described event or circumstance may or may not occur, and that the description includes instances where said event or circumstance occurs and instances in which it does not.

A "substituted" group includes embodiments in which a monoradical substituent is bound to a single atom of the substituted group (e.g. forming a branch), and also includes embodiments in which the substituent may be a diradical bridging group bound to two adjacent atoms of the substituted group, thereby forming a fused ring on the substituted group.

A compound of a given Formula (e.g. the "compound of Formula (I)") is intended to encompass the compounds of the invention as disclosed, and the pharmaceutically acceptable salts, pharmaceutically acceptable esters, hydrates, polymorphs, and prodrugs of such compounds. Additionally, the compounds of the invention may possess one or more asymmetric centers, and can be produced as a racemic mixture or as individual enantiomers or diastereoisomers. The number of stereoisomers present in any given compound of a given Formula depends upon the number of asymmetric centers present (there are 2n stereoisomers possible where n is the number of asymmetric centers). The individual stereoisomers may be obtained by resolving a racemic or non-racemic mixture of an intermediate at some appropriate stage of the synthesis, or by resolution of the compound by conventional means. The individual stereoisomers (including individual enantiomers and diastereoisomers) as well as racemic and non-racemic mixtures of stereoisomers are encompassed within the scope of the present invention, all of which are intended to be depicted by the structures of this specification unless otherwise specifically indicated.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn Ingold Prelog R S system. When the compound is a pure enantiomer the stereochemistry at each chiral carbon may be specified by either R or S. Resolved compounds whose absolute configuration is unknown are designated (+) or (−) depending on the direction (dextro- or laevorotary) that they rotate the plane of polarized light at the wavelength of the sodium D line.

The invention also included compounds of Formula I in which from 1 to n hydrogens attached to a carbon atom is/are replaced by deuterium, in which n is the number of hydrogens in the molecule. Such compounds exhibit increased resistance to metabolism, and are thus useful for increasing the half life of any compound of Formula I when administered to a mammal. See, for example, Foster, "Deuterium Isotope Effects in Studies of Drug Metabolism", Trends Pharmacol. Sci. 5(12):524-527 (1984). Such compounds are synthesized by means well known in the art, for example by employing starting materials in which one or more hydrogens have been replaced by deuterium.

Combination Therapy

Coronary patients being treated for an acute cardiovascular disease event by administration of late sodium channel blockers often exhibit diseases or conditions that benefit from treatment with other therapeutic agents. These diseases or conditions can be of the cardiovascular nature or can be related to pulmonary disorders, metabolic disorders, gastrointestinal disorders and the like. Additionally, some coronary patients being treated for an acute cardiovascular disease event by administration of late sodium channel blockers exhibit conditions that can benefit from treatment with therapeutic agents that are antibiotics, analgesics, and/or antidepressants and anti-anxiety agents.

Cardiovascular related diseases or conditions that can benefit from a combination treatment of late sodium channel blockers with other therapeutic agents include, without limitation, angina, including stable angina, unstable angina (UA), exercised-induced angina, variant angina, arrhythmias, intermittent claudication, myocardial infarction including non-STE myocardial infarction (NSTEMI), heart failure including congestive (or chronic) heart failure, acute heart failure, or recurrent ischemia.

Therapeutic agents suitable for treating cardiovascular related diseases or conditions include anti-anginals, heart failure agents, antithrombotic agents, antiarrhythmic agents, antihypertensive agents, and lipid lowering agents.

The co-administration of late sodium channel blockers with therapeutic agents suitable for treating cardiovascular related conditions allows enhancement in the standard of care therapy the patient is currently receiving.

Anti-anginals include beta-blockers, calcium channel blockers, and nitrates. Beta blockers reduce the heart's need for oxygen by reducing its workload resulting in a decreased heart rate and less vigorous heart contraction. Examples of beta-blockers include acebutolol (Sectral), atenolol (Tenormin), betaxolol (Kerlone), bisoprolol/hydrochlorothiazide (Ziac), bisoprolol (Zebeta), carteolol (Cartrol), esmolol (Brevibloc), labetalol (Normodyne, Trandate), metoprolol (Lopressor, Toprol XL), nadolol (Corgard), propranolol (Inderal), sotalol (Betapace), and timolol (Blocadren).

Nitrates dilate the arteries and veins thereby increasing coronary blood flow and decreasing blood pressure. Examples of nitrates include nitroglycerin, nitrate patches, isosorbide dinitrate, and isosorbide-5-mononitrate.

Calcium channel blockers prevent the normal flow of calcium into the cells of the heart and blood vessels causing the blood vessels to relax thereby increasing the supply of blood and oxygen to the heart. Examples of calcium channel blockers include amlodipine (Norvasc, Lotrel), bepridil (Vascor), diltiazem (Cardizem, Tiazac), felodipine (Plendil), nifedipine (Adalat, Procardia), nimodipine (Nimotop), nisoldipine (Sular), verapamil (Calan, Isoptin, Verelan), and nicardipine.

Agents used to treat heart failure include diuretics, ACE inhibitors, vasodilators, and cardiac glycosides. Diuretics eliminate excess fluids in the tissues and circulation thereby relieving many of the symptoms of heart failure. Examples of diuretics include hydrochlorothiazide, metolazone (Zaroxolyn), furosemide (Lasix), bumetanide (Bumex), spironolactone (Aldactone), and eplerenone (Inspra).

Angiotensin converting enzyme (ACE) inhibitors reduce the workload on the heart by expanding the blood vessels and decreasing resistance to blood flow. Examples of ACE inhibitors include benazepril (Lotensin), captopril (Capoten), enalapril (Vasotec), fosinopril (Monopril), lisinopril (Prinivil, Zestril), moexipril (Univasc), perindopril (Aceon), quinapril (Accupril), ramipril (Altace), and trandolapril (Mavik).

Vasodilators reduce pressure on the blood vessels by making them relax and expand. Examples of vasodilators include hydralazine, diazoxide, prazosin, clonidine, and methyldopa. ACE inhibitors, nitrates, potassium channel activators, and calcium channel blockers also act as vasodilators.

Cardiac glycosides are compounds that increase the force of the heart's contractions. These compounds strengthen the pumping capacity of the heart and improve irregular heartbeat activity. Examples of cardiac glycosides include digitalis, digoxin, and digitoxin.

Antithrombotics inhibit the clotting ability of the blood. There are three main types of antithrombotics—platelet inhibitors, anticoagulants, and thrombolytic agents.

Platelet inhibitors inhibit the clotting activity of platelets, thereby reducing clotting in the arteries. Examples of platelet inhibitors include acetylsalicylic acid (aspirin), ticlopidine, clopidogrel (plavix), dipyridamole, cilostazol, persantine sulfinpyrazone, dipyridamole, indomethacin, and glycoprotein llb/llla inhibitors, such as abciximab, tirofiban, and eptifibatide (Integrelin). Beta blockers and calcium channel blockers also have a platelet-inhibiting effect.

Anticoagulants prevent blood clots from growing larger and prevent the formation of new clots. Examples of anticoagulants include bivalirudin (Angiomax), warfarin (Coumadin), unfractionated heparin, low molecular weight heparin, danaparoid, lepirudin, and argatroban.

Thrombolytic agents act to break down an existing blood clot. Examples of thrombolytic agents include streptokinase, urokinase, and tenecteplase (TNK), and tissue plasminogen activator (t-PA).

Antiarrhythmic agents are used to treat disorders of the heart rate and rhythm Examples of antiarrhythmic agents include amiodarone, quinidine, procainamide, lidocaine, and propafenone. Cardiac glycosides and beta blockers are also used as antiarrhythmic agents.

Antihypertensive agents are used to treat hypertension, a condition in which the blood pressure is consistently higher than normal. Hypertension is associated with many aspects of cardiovascular disease, including congestive heart failure, atherosclerosis, and clot formation. Examples of antihypertensive agents include alpha-1-adrenergic antagonists, such as prazosin (Minipress), doxazosin mesylate (Cardura), prazosin hydrochloride (Minipress), prazosin, polythiazide (Minizide), and terazosin hydrochloride (Hytrin); beta-adrenergic antagonists, such as propranolol (Inderal), nadolol (Corgard), timolol (Blocadren), metoprolol (Lopressor), and pindolol (Visken); central alpha-adrenoceptor agonists, such as clonidine hydrochloride (Catapres), clonidine hydrochloride and chlorthalidone (Clorpres, Combipres), guanabenz Acetate (Wytensin), guanfacine hydrochloride (Tenex), methyldopa (Aldomet), methyldopa and chlorothiazide (Aldoclor), methyldopa and hydrochlorothiazide (Aldoril); combined alpha/beta-adrenergic antagonists, such as labetalol (Normodyne, Trandate), Carvedilol (Coreg); adrenergic neuron blocking agents, such as guanethidine (Ismelin), reserpine (Serpasil); central nervous system-acting antihypertensives, such as clonidine (Catapres), methyldopa (Aldomet), guanabenz (Wytensin); anti-angiotensin II agents; ACE inhibitors, such as perindopril (Aceon) captopril (Capoten), enalapril (Vasotec), lisinopril (Prinivil, Zestril); angiotensin-II receptor antagonists, such as Candesartan (Atacand), Eprosartan (Teveten), Irbesartan (Avapro), Losartan (Cozaar), Telmisartan (Micardis), Valsartan (Diovan); calcium channel blockers, such as verapamil (Calan, Isoptin), diltiazem (Cardizem), nifedipine (Adalat, Procardia); diuretics; direct vasodilators, such as nitroprusside (Nipride), diazoxide (Hyperstat IV), hydralazine (Apresoline), minoxidil (Loniten), verapamil; and potassium channel activators, such as aprikalim, bimakalim, cromakalim, emakalim, nicorandil, and pinacidil.

Lipid lowering agents are used to lower the amounts of cholesterol or fatty sugars present in the blood. Examples of lipid lowering agents include bezafibrate (Bezalip), ciprofibrate (Modalim), and statins, such as atorvastatin (Lipitor), fluvastatin (Lescol), lovastatin (Mevacor, Altocor), mevastatin, pitavastatin (Livalo, Pitava) pravastatin (Lipostat), rosuvastatin (Crestor), and simvastatin (Zocor).

In this invention, the patient in need of the late sodium channel blocker often suffers from secondary medical conditions such as one or more of a metabolic disorder, a pulmonary disorder, a peripheral vascular disorder, or a gastrointestinal disorder. Such patients can benefit from treatment of a combination therapy comprising administering to the patient the compounds of the invention in combination with at least one therapeutic agent.

Pulmonary disorder refers to any disease or condition related to the lungs. Examples of pulmonary disorders include, without limitation, asthma, chronic obstructive pulmonary disease (COPD), bronchitis, and emphysema.

Examples of therapeutics agents used to treat pulmonary disorders include bronchodilators including beta2 agonists and anticholinergics, corticosteroids, and electrolyte supplements. Specific examples of therapeutic agents used to treat pulmonary disorders include epinephrine, terbutaline (Brethaire, Bricanyl), albuterol (Proventil), salmeterol (Serevent, Serevent Diskus), theophylline, ipratropium bromide (Atrovent), tiotropium (Spiriva), methylprednisolone (Solu-Medrol, Medrol), magnesium, and potassium.

Examples of metabolic disorders include, without limitation, diabetes, including type I and type II diabetes, metabolic syndrome, dyslipidemia, obesity, glucose intolerance, hypertension, elevated serum cholesterol, and elevated triglycerides.

Examples of therapeutic agents used to treat metabolic disorders include antihypertensive agents and lipid lowering agents, as described in the section "Cardiovascular Agent Combination Therapy" above. Additional therapeutic agents used to treat metabolic disorders include insulin, sulfonylureas, biguanides, alpha-glucosidase inhibitors, and incretin mimetics.

Peripheral vascular disorders are disorders related to the blood vessels (arteries and veins) located outside the heart and brain, including, for example peripheral arterial disease (PAD), a condition that develops when the arteries that supply blood to the internal organs, arms, and legs become completely or partially blocked as a result of atherosclerosis.

Gastrointestinal disorders refer to diseases and conditions associated with the gastrointestinal tract. Examples of gastrointestinal disorders include gastroesophageal reflux disease (GERD), inflammatory bowel disease (IBD), gastroenteritis, gastritis and peptic ulcer disease, and pancreatitis.

Examples of therapeutic agents used to treat gastrointestinal disorders include proton pump inhibitors, such as pantoprazole (Protonix), lansoprazole (Prevacid), esomeprazole (Nexium), omeprazole (Prilosec), rabeprazole; H2 blockers, such as cimetidine (Tagamet), ranitidine (Zantac), famotidine (Pepcid), nizatidine (Axid); prostaglandins, such as misoprostoL (Cytotec); sucralfate; and antacids.

Patients presenting with an acute coronary disease event may exhibit conditions that benefit from administration of therapeutic agent or agents that are antibiotics, analgesics, antidepressant and anti-anxiety agents in combination with ranolazine.

Antibiotics are therapeutic agents that kill, or stop the growth of, microorganisms, including both bacteria and fungi. Example of antibiotic agents include β-Lactam antibiotics, including penicillins (amoxicillin), cephalosporins, such as cefazolin, cefuroxime, cefadroxil (Duricef), cephalexin (Keflex), cephradine (Velosef), cefaclor (Ceclor), cefuroxime axtel (Ceftin), cefprozil (Cefzil), loracarbef (Lorabid), cefixime (Suprax), cefpodoxime proxetil (Vantin), ceftibuten (Cedax), cefdinir (Omnicef), ceftriaxone (Rocephin), carbapenems, and monobactams; tetracyclines, such as tetracycline; macrolide antibiotics, such as erythromycin; aminoglycosides, such as gentamicin, tobramycin, amikacin; quinolones such as ciprofloxacin; cyclic peptides, such as vancomycin, streptogramins, polymyxins; lincosamides, such as clindamycin; oxazolidinoes, such as linezolid; and sulfa antibiotics, such as sulfisoxazole.

Analgesics are therapeutic agents that are used to relieve pain. Examples of analgesics include opiates and morphinomimetics, such as fentanyl and morphine; paracetamol; NSAIDs, and COX-2 inhibitors.

Antidepressant and anti-anxiety agents include those agents used to treat anxiety disorders, depression, and those used as sedatives and tranquillers. Examples of antidepressant and anti-anxiety agents include benzodiazepines, such as diazepam, lorazepam, and midazolam; enzodiazepines; barbiturates; glutethimide; chloral hydrate; meprobamate; sertraline (Zoloft, Lustral, Apo-Sertral, Asentra, Gladem, Serlift, Stimuloton); escitalopram (Lexapro, Cipralex); fluoxetine (Prozac, Sarafem, Fluctin, Fontex, Prodep, Fludep, Lovan); venlafaxine (Effexor XR, Efexor); citalopram (Celexa, Cipramil, Talohexane); paroxetine (Paxil, Seroxat, Aropax); trazodone (Desyrel); amitriptyline (Elavil); and bupropion (Wellbutrin, Zyban).

The term "therapeutically effective amount" refers to an amount that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "treatment" or "treating" means any treatment of a disease in a mammal, including:

(i) preventing the disease, that is, causing the clinical symptoms of the disease not to develop;

(ii) inhibiting the disease, that is, arresting the development of clinical symptoms; and/or (iii) relieving the disease, that is, causing the regression of clinical symptoms.

In many cases, the compounds of this invention are capable of forming acid and/or base salts by virtue of the presence of amino and/or carboxyl groups or groups similar thereto.

The term "pharmaceutically acceptable salt" of a given compound refers to salts that retain the biological effectiveness and properties of the given compound, and which are not biologically or otherwise undesirable. Pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

"Coronary diseases" or "cardiovascular diseases" refer to diseases of the cardiovasculature arising from any one or more than one of, for example, heart failure (including congestive heart failure, diastolic heart failure and systolic heart failure), acute heart failure, ischemia, recurrent ischemia, myocardial infarction, arrhythmias, angina (including exercise-induced angina, variant angina, stable angina, unstable angina), acute coronary syndrome, diabetes, and intermittent claudication.

"Intermittent claudication" means the pain associated with peripheral artery disease. "Peripheral artery disease" or PAD is a type of occlusive peripheral vascular disease (PVD). PAD affects the arteries outside the heart and brain. The most common symptom of PAD is a painful cramping in the hips, thighs, or calves when walking, climbing stairs, or exercising. The pain is called intermittent claudication. When listing the symptom intermittent claudication, it is intended to include both PAD and PVD Arrhythmia refers to any abnormal heart rate. Bradycardia refers to abnormally slow heart rate whereas tachycardia refers to an abnormally rapid heart rate. As used herein, the treatment of arrhythmia is intended to include the treatment of supra ventricular tachycardias such as atrial fibrillation, atrial flutter, AV nodal reentrant tachycardia, atrial tachycardia, and the ventricular tachycardias (VTs), including idiopathic ventricular tachycardia, ventricular fibrillation, pre-excitation syndrome, and Torsade de Pointes (TdP), Where a given group (moiety) is described herein as being attached to a second group and the site of attachment is not explicit, the given group may be attached at any available site of the given group to any available site of the second group. For example, a "lower alkyl-substituted phenyl", where the attachment sites are not explicit, may have any available site of the lower alkyl group attached to any available site of the phenyl group. In this regard, an "available site" is a site of the group at which a hydrogen of the group may be replaced with a substituent.

Nomenclature

Names of compounds of the present invention are provided using ACD/Name software for naming chemical compounds (Advanced Chemistry Development, Inc., Toronto). Other compounds or radicals may be named with common names, or systematic or non-systematic names. The naming and numbering of the compounds of the invention is illustrated with a representative compound of Formula I

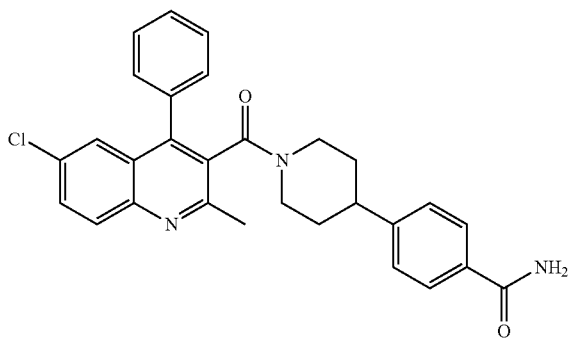 [SMILES: Cc1nc2ccc(Cl)cc2c(-c2ccccc2)c1C(=O)N1CCC(c2ccc(C(N)=O)cc2)CC1]

which is named 4-(1-(6-chloro-2-methyl-4-phenylquinoline-3-carbonyl)piperidin-4-yl)benzamide.

DETAILED DESCRIPTION OF THE INVENTION

The present invention provides novel compounds of Formula (I) that function as late sodium channel blockers:

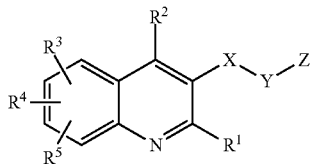

Formula (I)

wherein:
$R^1$ is amino or alkyl of 1-6 carbon atoms optionally substituted by halo, alkoxy of 1-6 carbon atoms, or phenoxy optionally substituted by 1, 2, or 3 substituents independently chosen from halo, alkyl of 1-6 carbon atoms, and alkoxy of 1-6 carbon atoms; or
$R^1$ is alkyl of 1-6 carbon atoms substituted by —$NR^6R^7$, in which $R^6$ and $R^7$ are independently chosen from hydrogen or alkyl of 1-6 carbon atoms, or $R^6$ and $R^7$ when combined with the nitrogen atom to which they are attached is a nitrogen-bearing heterocycle or heteroaryl group;
$R^2$ is alkyl of 1-6 carbon atoms, phenyl, or heteroaryl, all of which are optionally substituted by halo, alkyl of 1-6 carbon atoms, hydroxyl, cyano, alkoxy of 1-6 carbon atoms, or —C(O)R, in which R is alkoxy of 1-6 carbon atoms or —$NR^6R^7$, in which $R^6$ and $R^7$ are independently chosen from hydrogen or alkyl of 1-6 carbon atoms;
$R^3$, $R^4$, and $R^5$ are independently chosen from hydrogen, halo, alkyl of 1-6 carbon atoms, hydroxyl, cyano, or alkoxy of 1-6 carbon atoms;
X is a covalent bond, cyano, —C(O)—, —C(O)O—, —CH(OH)—, or —C(O)$NR^6R^7$;

Y is a covalent bond, alkylene of 1-6 carbon atoms, or heteroaryl;
Z is a covalent bond, hydrogen, phenyl, benzyl, or cycloalkyl of 3-8 carbon atoms, all of which are optionally substituted by phenyl or heteroaryl, both of which are optionally substituted by 1, 2, or 3 substituents independently chosen from halo, alkyl of 1-6 carbon atoms, alkoxy of 1-6 carbon atoms, and —C(O)$R^8$, where $R^8$ is alkyl of 1-6 carbon atoms, alkoxy of 1-6 carbon atoms, or —$NR^6R^7$, in which $R^6$ and $R^7$ are independently chosen from hydrogen or alkyl of 1-6 carbon atoms; or
Z is phenyl optionally substituted by 1, 2, or 3 substituents independently chosen from halo, alkyl of 1-6 carbon atoms optionally substituted by heteroaryl, and alkoxy of 1-6 carbon atoms;
with the proviso that X, Y and Z cannot all be covalent bonds; and the pharmaceutically acceptable salts, esters, prodrugs, or solvates thereof.

One embodiment of the invention includes compounds in which $R^1$ is alkyl of 1-6 carbon atoms, particularly where $R^1$ is methyl, $R^2$ is alkyl of 1-3 carbon atoms or phenyl optionally substituted by halo, and $R^3$, $R^4$, and $R^5$ are hydrogen or halo. A subgroup of this embodiment of the invention includes compounds in which X is a covalent bond, —C(O)O—, or heteroaryl, Y is methylene, and Z is cycloalkyl, phenyl, or benzyl, all of which are optionally substituted by halo or heteroaryl.

Another embodiment of the invention includes compounds in which $R^1$ is methyl substituted by ethoxy, 4-chloro-2-methoxyphenyl, or —$NR^6R^7$, where $R^6$ and $R^7$ are both methyl, or $R^6$ and $R^7$ when combined with the nitrogen atom to which they are attached are pyrrolidine-2,5-dione, isoindoline-1,3-dione, imidazolyl, or tetrazolyl, $R^2$ is methyl or phenyl optionally substituted by halo; and X is —C(O)— or —C(O)O—, particularly where $R^3$, $R^4$, and $R^5$ are hydrogen or halo.

Another embodiment of the invention includes compounds in which $R^1$ is methyl and $R^2$ is methyl or phenyl optionally substituted by halo.

Compounds within the scope of the invention include, but are not limited to:
2-bromobenzyl 2,4-dimethylquinoline-3-carboxylate;
benzyl 2-methyl-4-phenylquinoline-3-carboxylate;
4-chlorobenzyl 2,4-dimethylquinoline-3-carboxylate;
2-(2-(4-chlorophenyl)propan-2-yl)-5-(2,4-dimethylquinolin-3-yl)-1,3,4-oxadiazole.
cyclopropylmethyl 6-chloro-2-methyl-4-phenylquinoline-3-carboxylate;
4-((1H-pyrazol-1-yl)methyl)benzyl 6-chloro-2-methyl-4-phenylquinoline-3-carboxylate;
ethyl 6-chloro-2-((4-chloro-2-methoxyphenoxy)methyl)-4-phenylquinoline-3-carboxylate;
ethyl 6-chloro-2-((1,3-dioxoisoindolin-2-yl)methyl)-4-phenylquinoline-3-carboxylate;
ethyl 2-((1H-imidazol-1-yl)methyl)-6-chloro-4-phenylquinoline-3-carboxylate;
ethyl 6-chloro-2-((2,5-dioxopyrrolidin-1-yl)methyl)-4-phenylquinoline-3-carboxylate;
ethyl 2-((1H-tetrazol-1-yl)methyl)-6-chloro-4-phenylquinoline-3-carboxylate;
ethyl 6-chloro-2-[(1,3-dioxo-1,3-dihydro-2H-isoindol-2-yl)methyl]-4-phenylquinoline-3-carboxylate;
ethyl 6-chloro-2-(1H-imidazol-1-ylmethyl)-4-phenylquinoline-3-carboxylate;
ethyl 6-chloro-2-[(2,5-dioxopyrrolidin-1-yl)methyl]-4-phenylquinoline-3-carboxylate;

ethyl 6-chloro-4-phenyl-2-(1H-tetrazol-1-ylmethyl)quinoline-3-carboxylate;
ethyl 6-chloro-2-[(4-chloro-2-methoxyphenoxy)methyl]-4-phenylquinoline-3-carboxylate;
ethyl 6-chloro-2-[(dimethylamino)methyl]-4-phenylquinoline-3-carboxylate;
ethyl 2-(ethoxymethyl)-4-methylquinoline-3-carboxylate;
(6-chloro-2-methyl-4-phenylquinolin-3-yl)(piperidin-1-yl)methanone;
4-(1-(6-chloro-2-methyl-4-phenylquinoline-3-carbonyl)piperidin-4-yl)benzamide;
(R)-1-phenylethyl 6-chloro-2-methyl-4-phenylquinoline-3-carboxylate;
(S)-1-phenylethyl 6-chloro-2-methyl-4-phenylquinoline-3-carboxylate;
4-((1H-pyrazol-1-yl)methyl)benzyl 6-chloro-2-methyl-4-phenylquinoline-3-carboxylate;
1-(6-chloro-2-methyl-4-phenylquinolin-3-yl)ethanol;
2-(2-(4-chlorophenyl)propan-2-yl)-5-(2,4-dimethylquinolin-3-yl)-1,3,4-oxadiazole;
benzyl 2-methyl-4-phenylquinoline-3-carboxylate;
tert-butyl 6-chloro-2-methyl-4-phenylquinoline-3-carboxylate;
6-chloro-N-(4-fluorobenzyl)-2-methyl-4-phenylquinoline-3-carboxamide;
6-chloro-3-[5-(4-chlorobenzyl)-1,3,4-oxadiazol-2-yl]-2-methyl-4-phenylquinoline;
cyclopropyl(phenyl)methyl 6-chloro-2-methyl-4-phenylquinoline-3-carboxylate;
(6-chloro-2-methyl-4-phenylquinolin-3-yl)(piperidin-1-yl)methanone;
(1S)-1-phenylethyl 6-chloro-2-methyl-4-phenylquinoline-3-carboxylate;
(1R)-1-phenylethyl 6-chloro-2-methyl-4-phenylquinoline-3-carboxylate;
cyclopropylmethyl 6-chloro-2-methyl-4-phenylquinoline-3-carboxylate;
4-{1-[(6-chloro-2-methyl-4-phenylquinolin-3-yl)carbonyl]piperidin-4-yl}benzamide;
4-(1H-pyrazol-1-ylmethyl)benzyl 6-chloro-2-methyl-4-phenylquinoline-3-carboxylate;
4-chlorobenzyl 2,4-dimethylquinoline-3-carboxylate;
tert-butyl 6-chloro-4-(2-chlorophenyl)-2-methylquinoline-3-carboxylate;
ethyl 6-chloro-4-(2-chlorophenyl)-2-methylquinoline-3-carboxylate;
tert-butyl 6-chloro-4-(2-fluorophenyl)-2-methylquinoline-3-carboxylate;
2-bromobenzyl 6-chloro-4-(2-chlorophenyl)-2-methylquinoline-3-carboxylate;
2-bromobenzyl 2,4-dimethylquinoline-3-carboxylate;
ethyl 6-chloro-2-methyl-4-phenylquinoline-3-carboxylate;
ethyl 6-chloro-4-(2-fluorophenyl)-2-methylquinoline-3-carboxylate; and
3-{5-[2-(4-chlorophenyl)propan-2-yl]-1,3,4-oxadiazol-2-yl}-2,4-dimethylquinoline.

The compounds provided by the present invention are effective in the treatment of conditions known to respond to administration of late sodium channel blockers, including cardiovascular diseases such as atrial and ventricular arrhythmias, Prinzmetal's (variant) angina, stable angina, unstable angina, ischemia and reperfusion injury in cardiac, kidney, liver and the brain, exercise induced angina, congestive heart disease, and myocardial infarction. The compounds provided by the present invention may be used in the treatment of diseases affecting the neuromuscular system resulting in pain, seizures, or paralysis, or in the treatment of diabetes and disease states related to diabetes, such as diabetic peripheral neuropathy, and neuropathic pain. Also included are central nervous system disorders such as acute, chronic, neuropathic, or inflammatory pain, migraine, cluster headaches, trigeminal neuralgia, herpetic neuralgia, general neuralgias, epilepsy or epilepsy conditions, and neurodegenerative disordes.

Pharmaceutical Compositions

Compounds provided in accordance with the present invention are usually administered in the form of pharmaceutical compositions. This invention therefore provides pharmaceutical compositions that contain, as the active ingredient, one or more of the compounds described, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The pharmaceutical compositions may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.)

The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parenteral, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound according to the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of compounds in accordance with the invention. Administration may be via capsule or enteric coated tablets, or the like. In making the pharmaceutical compositions that include at least one compound described herein, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. Preferably, for oral administration, each dosage unit contains from 1 mg to 2 g of a compound described herein, and for parenteral administration, preferably from 0.1 to 700 mg of a compound a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Synthetic Reaction Parameters

The terms "solvent," "inert organic solvent" or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Unless specified to the contrary, the solvents used in the reactions of the present invention are inert organic solvents, and the reactions are carried out under an inert gas, preferably nitrogen.

The term "q.s." means adding a quantity sufficient to achieve a stated function, e.g., to bring a solution to the desired volume (i.e., 100%).

Synthesis of the Compounds of Formula (I)

One method of preparing the compounds of Formula (I) is shown in Reaction Scheme I.

REACTION SCHEME I in which $R^1$, $R^2$, $R^3$, $R^4$, and $R^5$ are as defined above, and R is —O-alkyl, —O-benzyl, or —$NR^6R^7$.

Typically, a compound of formula (1) in an inert solvent, for example methanol or ethanol, is contacted with a compound of formula (2) in the presence of a tertiary base, for example triethylamine, and the mixture heated at about 60-90° C. for about 10-24 hours. When the reaction is substantially complete, the product of Formula (I) is isolated by conventional means, for example by filtration of the precipitated product.

A preparation of a compound of formula (2) in which R is —$NR^6R^7$ is shown in Reaction Scheme II.

REACTION SCHEME II in which R is $NR^6R^7$

Typically, to a solution of the amine of formula B in an inert solvent at about room temperature is added the compound of formula A (4-methyleneoxetan-2-one), and the reaction maintained at that temperature for about 10-24 hours. When the reaction is substantially complete, the product of formula (2) in which R is —$NR^6R^7$ is isolated by conventional means.

A preparation of a compound of formula (2) in which R is optionally substituted —O-alkyl or optionally substituted —O-benzyl is shown in Reaction Scheme III.

REACTION SCHEME III in which R is alkoxy or benzyloxy

Typically, to a solution of the compound of formula C in an inert solvent, for example tetrahydrofuran, at about room temperature is added a hindered tertiary base, for example 4-(N,N-dimethylamino)pyridine followed by the compound of formula A (4-methyleneoxetan-2-one), and the reaction mixture maintained at that temperature for about 4-24 hours. When the reaction is substantially complete, the product of formula (2) in which R is optionally substituted alkoxy or optionally substituted benzyloxy is isolated by conventional means.

The preparation of compounds of Formula (I) varying the $R^1$ groups can proceed from a 2-chloromethyl intermediate. An example of the preparation of such an intermediate is shown in Reaction Scheme IV

REACTION SCHEME IV

Typically, to a solution of the compound of formula (1) in an inert solvent, for example ethanol at about room temperature, is added the compound of formula (2) followed by ytterbium triflate, and the mixture maintained at about room temperature for about 24-72 hours. When the reaction is substantially complete, the product of formula (3) is isolated by conventional means.

The chloromethyl compound of formula (3) is then converted to a compound of Formula (I) by conventional syntheses. An example of such a preparation is shown in Reaction Scheme V.

REACTION SCHEME V

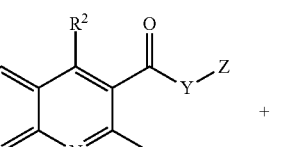

-continued

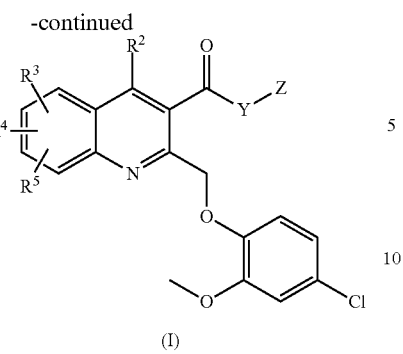

To a solution of the compound of formula (2) in an inert solvent, for example N,N-dimethylformamide at about room temperature is added the compound of formula (4) followed by a metal hydride, for example sodium hydride, and the mixture stirred at about temperature for about 10-48 hours. When the reaction is substantially complete, the product of Formula (I) is isolated by conventional means.

Similarly, reaction of (3) with other compounds with a labile hydrogen produces other compounds of Formula (I), varying $R^1$.

The compounds of the invention are prepared using methods disclosed herein and routine modifications thereof which will be apparent given the disclosure herein and methods well known in the art. Conventional and well-known synthetic methods may be used in addition to the teachings herein. Reagents may be purchased commercially, e.g. from Sigma Aldrich or other chemical suppliers.

Example 1

A. Preparation of 1-(piperidin-1-yl)butane-1,3-dione

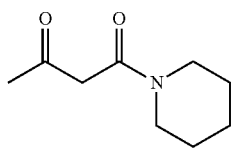

To a solution of piperidine (4.94 ml, 50 mmol) in dry tetrahydrofuran (100 ml) at room temperature was added 4-methyleneoxetan-2-one (3.8 ml, 50 mmol) dropwise. The reaction mixture was stirred for 24 hours at room temperature, then the solvent removed under reduced pressure and the residue dissolved in ethyl acetate. The organic phase was poured into a separatory funnel and washed with 1M aqueous hydrochloric acid, water, saturated aqueous sodium bicarbonate and brine. The organic phase was separated and the solvent removed under reduced pressure to provide 1-(piperidin-1-yl)butane-1,3-dione (8.5 g, 100%) as a viscous oil. $^1$H NMR (CDCl$_3$, 400 MHz) δ 3.56 (2H, app t); 3.54 (s, 2H); 3.24 (2H, app t); 2.28 (s, 3H); 1.70-1.5 (m, 6H). The compound was utilized in the next reaction without purification.

B. Similarly, following the procedure of Example 1A, but substituting other amines in place of piperidine, other beta-ketoamides were prepared, for example:

4-(1-(3-oxobutanoyl)piperidin-4-yl)benzamide; (11.5 g, 74%) as a white powder. LCMS (CI) M+H 289.

Example 2

A. Preparation of (R)-1-phenylethyl 3-oxobutanoate

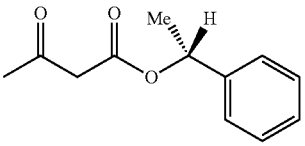

To a solution of (R)-1-phenylethanol (6.0 ml, 50 mmol) in dry tetrahydrofuran (75 ml) at room temperature was added 4-(N,N-dimethylamino)pyridine (610 mg, 5.0 mmol) followed by dropwise addition of 4-methyleneoxetan-2-one (3.83 ml, 50 mmol). The reaction was stirred for 12 hours at room temperature, then the solvent removed under reduced pressure. The residue was dissolved in ethyl acetate, poured into a separatory funnel, and washed with 1M aqueous hydrochloric acid, water, saturated aqueous sodium bicarbonate, then brine. The organic phase was separated and the solvent removed under resuced pressure to provide (R)-1-phenylethyl 3-oxobutanoate as a light reddish oil (10.3 g, 100%). $^1$H NMR (CDCl$_3$, 400 MHz) δ 7.4-7.2 (m, 5H); 5.94 (q, 1H, J=6.6 Hz); 3.45 (s, 2H); 2.22 (s, 3H); 1.56 (d, 3H, J=6.6 Hz).

Similarly, following the procedure of Example 2A, but substituting other alcohols in place of (R)-1-phenylethanol, other compounds of formula (2) are prepared. For example:

4-((1H-pyrazol-1-yl)methyl)benzyl 3-oxobutanoate; (7.2 g, 100%). $^1$H NMR (CDCl$_3$, 400 MHz) δ 7.92 (d, 1H, J=2.3 Hz); 7.74-7.67 (m, 1H); 7.70 (d, 2H, J=8.6 Hz); 7.45 (d, 2H, J=8.6 Hz); 7.58 (t, 1H, J=2.3 Hz); 5.35 (s, 2H); 5.18 (s, 2H); 3.4 (s, 2H); 2.25 (s, 3H).

Example 3

Preparation of a Compound of Formula (I)

A. Preparation of (6-chloro-2-methyl-4-phenylquinolin-3-yl)(piperidin-1-yl)methanone

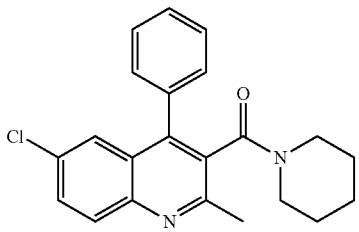 [SMILES: Cc1nc2ccc(Cl)cc2c(-c2ccccc2)c1C(=O)N1CCCCC1]

To a solution of 1-(piperidin-1-yl)butane-1,3-dione (1.08 g, 6.5 mmol) in ethanol (20 ml) at room temperature was added 2-amino-5-chlorophenylacetophenone (1.16 g 5.0 mmol) followed by ytterbium triflate (294 mg, 0.5 mmol). The reaction mixture was stirred at room temperature for 12 hours. The white powdery precipitate that was formed in the reaction mixture was filtered off, washed with ethanol, and dried under reduced pressure to provide (6-chloro-2-methyl-4-phenylquinolin-3-yl)(piperidin-1-yl)methanone (874 mg, 48%) as a white powder. $^1$H NMR (CDCl$_3$, 400 MHz) δ 8.1 (d, 1H, J=8.6 Hz); 7.67 (dd, 1H, J=8.6, 2.3 Hz); 7.63 (d, 1H, J=2.3 Hz); 7.6-7.5 (m, 4H); 7.33-7.28 (m, 1H); 3.55 (ddd, 1H, J=13.3, 7.4, 3.1 Hz); 3.37 (ddd, 1H, J=13.3, 7.4, 3.1 Hz); 3.05 (ddd, 1H, J=13.3, 7.4, 3.1 Hz); 2.80 (ddd, 1H, J=13.3, 7.4, 3.1 Hz); 2.77 (s, 3H); 1.60-1.2 (m, 5H); 1.0 (m, 1H). LC MS (CI) shows M+H 365.

Similarly, following the procedure of Example 3A, replacing 1-(piperidin-1-yl)butane-1,3-dione with 4-(1-(3-oxobutanoyl)piperidin-4-yl)benzamide, 4-(1-(3-oxobutanoyl)piperidin-4-yl)benzamide was prepared; (1.1 g, 76%) as a free flowing white powder. ¹H NMR (DMSO-d6, 400 MHz) 3:1 Rotameric forms complicates spectrum, the major rotamer is described; δ 8.09 (d, 1H, J=8.9 Hz); 7.9 (bs, NH, 1H); 7.8 (m, 3H); 7.7-7.5 (m, 6H); 7.25 (bs, NH, 1H); 6.8 (app d, 2H); 4.5 (d, 1H, J=12.9 Hz); 3.4-3.3 (m, 1H); 3.38 (s, 3H); 3.13 (app t, 1H, J=12.9 Hz); 2.8-2.4 (m, 2H); 2.5 (s, 3H); 0.72 (m, 1H); 0.54 (m, 1H). LC MS (CI) shows M+H 484.

Example 4

Preparation of a Compound of Formula (I)

A. Preparation of 4-(1-(6-chloro-2-methyl-4-phenylquinoline-3-carbonyl)piperidin-4-yl)benzamide

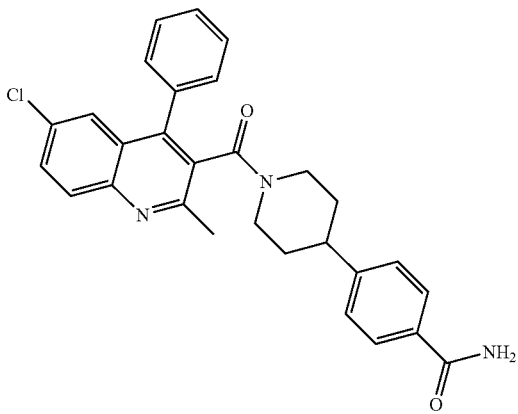 [SMILES: Cc1nc2ccc(Cl)cc2c(-c2ccccc2)c1C(=O)N1CCC(c2ccc(C(N)=O)cc2)CC1]

To a solution of (2-amino-5-chlorophenyl)(phenyl)methanone (693 mg, 3.0 mmol) in ethanol (10 ml) was added 4-(1-(3-oxobutanoyl)piperidin-4-yl)benzamide (893 mg, 3.1 mmol) followed by ytterbium triflate (186 mg, 0.3 mmol). The mixture was heated at 82° C. for 12 hours. The reaction mixture was cooled to room temperature, and the white powder thus obtained was filtered off, washed with ethanol, ethyl acetate, and finally ether to provide 4-(1-(6-chloro-2-methyl-4-phenylquinoline-3-carbonyl)piperidin-4-yl)benzamide (1.1 g, 76%) as a free flowing white powder. ¹H NMR (DMSO-d6, 400 MHz) δ: 1 Rotameric forms complicates spectrum, the major rotamer is described; δ 8.09 (d, 1H, J=8.9 Hz); 7.9 (bs, NH, 1H); 7.8 (m, 3H); 7.7-7.5 (m, 6H); 7.25 (bs, NH, 1H); 6.8 (app d, 2H); 4.5 (d, 1H, J=12.9 Hz); 3.4-3.3 (m, 1H); 3.38 (s, 3H); 3.13 (app t, 1H, J=12.9 Hz); 2.8-2.4 (m, 2H); 2.5 (s, 3H); 0.72 (m, 1H); 0.54 (m, 1H). LC MS (CI) shows M+H 484.

Example 5

Preparation of a Compound of Formula (I)

A. Preparation of (R)-1-phenylethyl 6-chloro-2-methyl-4-phenylquinoline-3-carboxylate

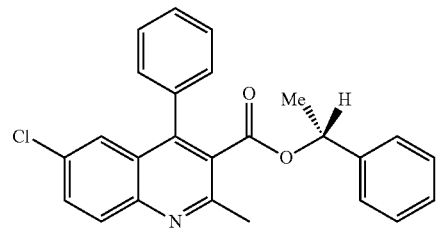 [SMILES: Cc1nc2ccc(Cl)cc2c(-c2ccccc2)c1C(=O)O[C@H](C)c1ccccc1]

To a solution of (2-amino-5-chlorophenyl)(phenyl)methanone (1.16 g, 5.0 mmol) in ethanol (20 ml) was added (R)-1-phenylethyl 3-oxobutanoate (1.3 g, 6.5 mmol) followed by ytterbium triflate (294 mg, 0.5 mmol). The mixture was stirred at room temperature for 12 hours, then the ethanol was removed under reduced pressure, and the residual viscous oil dissolved in ethyl acetate. The organic phase was poured into a separatory funnel and washed with 1M aqueous hydrochloric acid, water, then brine. The organic phase was seoarated, and the solvent was removed under reduced pressure to provide a viscous oil. This was dissolved in a small amount of diethyl ether, and the solution allowed to stand at room temperature overnight. The white precipitate formed was filtered, washed with cold diethyl ether, and dried under reduced pressure, to provide (R)-1-phenylethyl 6-chloro-2-methyl-4-phenylquinoline-3-carboxylate (1.33 g, 67%) as a white powder. Rf=0.26 using 80:20 hexanes:ethyl acetate eluent on glass backed silica gel plates. ¹H NMR (CDCl₃, 400 MHz) δ 8.98 (d, 1H, J=8.9 Hz); 7.96 (d, 1H, J=7.4 Hz); 7.72 (d, 1H, J=1.95 Hz); 7.6-7.1 (m, 10H); 5.88 (q, 1H, J=6.6 Hz); 3.05 (s, 3H); 1.3 (d, 3H, J=6.6 Hz). LC MS (CI) shows M+H 402.

Similarly, following the procedure of Example 5A above, but using (S)-1-phenylethyl 3-oxobutanoate in place of (R)-1-phenylethyl 3-oxobutanoate, (S)-1-phenyl ethyl 6-chloro-2-methyl-4-phenylquinoline-3-carboxylate was prepared.

Similarly, following the procedure of Example 5A above, but using 4-((1H-pyrazol-1-yl)methyl)benzyl 3-oxobutanoate in place of (R)-1-phenylethyl 3-oxobutanoate, 4-((1H-pyrazol-1-yl)methyl)benzyl 6-chloro-2-methyl-4-phenylquinoline-3-carboxylate was prepared as a light tan powder. Rf=0.41 using 1:1 ethyl acetate:hexanes eluent on a glass backed silica gel plate. ¹H NMR (CDCl₃, 400 MHz) shows about 15% rotamer δ 9.1 (d, 1H, J=8.9 Hz); 7.96 (dd, 1H, J=8.9, 2.3 Hz); 7.86 (d, 1H, J=1.95 Hz); 7.71 (d, 1H, J=2.3 Hz); 7.64-7.28 (m, 8H); 7.06 (d, 2H, J=8.2 Hz); 6.52 (bs, 1H); 5.53 (s, 2H); 5.1 (s, 2H); 3.43 (s, 3H). LC MS (CI) shows M+H 468.

Example 6

Preparation of a Compound of Formula (3)

A. Preparation of ethyl 6-chloro-2-(chloromethyl)-4-phenylquinoline-3-carboxylate

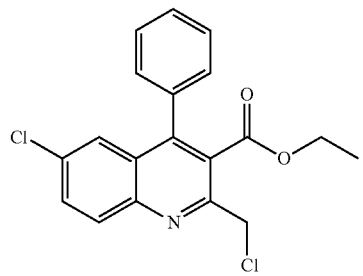 [SMILES: CCOC(=O)c1c(CCl)nc2ccc(Cl)cc2c1-c1ccccc1]

To a yellow solution of 2-amino-5-chlorobenzophenone (6.93 g, 30.0 mmol) in ethanol (150 ml) was added ethyl 4-chloroacetoacetate (5.3 ml, 39.0 mmol) followed by ytterbium triflate (1.6 g, 3.0 mmol). The mixture was stirred at room temperature for 48 hours, at which time a voluminous white suspension was noted. The mixture was filtered, and the precipitate washed with ethanol, then diethyl ether, to provide ethyl 6-chloro-2-(chloromethyl)-4-phenylquinoline-3-carboxylate as a white powder (93%). $^1$H NMR (CDCl$_3$; 400 MHz) δ 8.08 (d, 1H, J=8.9 Hz); 7.71 (dd, 1H, J=8.9, 2.3 Hz); 7.59 (d, 1H, J=1.95 Hz); 7.54 (m, 3H); 7.38-7.30 (m, 2H); 5.0 (s, 2H); 4.05 (q, 2H, J=7.0 Hz); 0.92 (t, 3H, J=7.0 Hz). LC MS (CI) shows M+H 360.

Example 7

Preparation of a Compound of Formula (I)

A. Preparation of ethyl 6-chloro-2-((4-chloro-2-methoxyphenoxy)methyl)-4-phenylquinoline-3-carboxylate

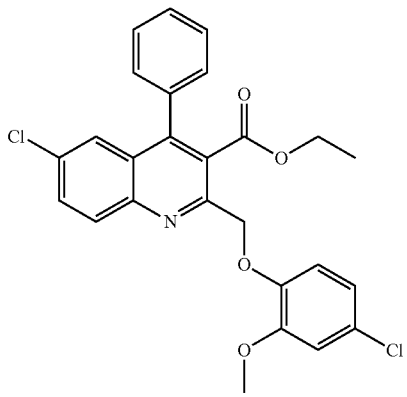 [SMILES: CCOC(=O)c1c(COc2ccc(Cl)cc2OC)nc2ccc(Cl)cc2c1-c1ccccc1]

To a solution of ethyl 6-chloro-2-(chloromethyl)-4-phenylquinoline-3-carboxylate (718 mg, 2.0 mmol) in dry N,N-dimethylformamide (3.0 ml) at room temperature was added 4-chloro-2-methoxyphenol (0.301 ml, 2.2 mmol) followed by sodium hydride (88.0 mg of a 60% oil dispersion, 2.2 mol). The mixture was stirred at room temperature for 18 hours, then the reaction mixture was diluted with ethyl acetate and poured into a separatory funnel. The organic phase was washed with saturated sodium bicarbonate and water (2×), then brine. The organic phase was separated, and the solvent removed under reduced pressure to provide a viscous oil. Upon sitting at room temperature overnight a solid formed, to which a mixture of 10% ethyl acetate/hexanes was added, and the resulting solid filtered off. The solid was washed with 20% ethyl acetate/hexanes and dried under reduced pressure to provide ethyl 6-chloro-2-((4-chloro-2-methoxyphenoxy)methyl)-4-phenylquinoline-3-carboxylate then provided PT-011 (558 mg, 58%) as a light yellow powder. TLC Rf=0.38 in 30% ethyl cetate:hexanes on a glass backed silica gel plate. $^1$H NMR (CDCl$_3$, 400 MHz) δ 8.08 (d, 1H, J=8.9 Hz); 7.69 (dd, 1H, J=8.9, 2.3 Hz); 7.58 (d, 1H, J=2.3 Hz); 7.48-7.52 (m, 3H); 7.36-7.30 (m, 2H); 6.95-6.92 (app d, 1H, J=8.6 Hz); 6.75 (s, 1H); 6.78-6.70 (m, 1H); 5.50 (s, 2H); 3.90 (q, 2H, J=7.0 Hz); 3.80 (s, 3H); 0.82 (t, 3H, J=7.0 Hz). LC MS (CI) shows M+H 482.

Example 8

Preparation of a Compound of Formula (I)

A. Preparation of ethyl 6-chloro-2-((1,3-dioxoisoindolin-2-yl)methyl)-4-phenylquinoline-3-carboxylate

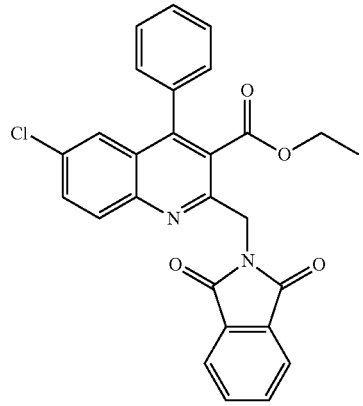 [SMILES: CCOC(=O)c1c(CN2C(=O)c3ccccc3C2=O)nc2ccc(Cl)cc2c1-c1ccccc1]

To a solution of ethyl 6-chloro-2-(chloromethyl)-4-phenylquinoline-3-carboxylate (539 mg, 1.5 mmol) in dry N,N-dimethylformamide (5 ml) at room temperature was added potassium phthalimide (278 mg, 1.5 mmol). The mixture was heated at 45° C. for 48 hours, then diluted with ethyl acetate and poured into a separatory funnel. The organic phase was washed with saturated sodium bicarbonate, water (2×), then brine. The organic phase was separated, and the solvent removed under reduced pressure, leaving a white solid, which was washed with a cold solution of 10% diethylether/hexanes, dried under reduced pressure, to provide ethyl 6-chloro-2-((1,3-dioxoisoindolin-2-yl)methyl)-4-phenylquinoline-3-carboxylate (580 mg, 82%) as a white powder. TLC Rf=0.41 using 1:1 ethyl acetate:hexanes eluent on a glass backed silica gel plate. $^1$H NMR (CDCl$_3$, 400 MHz) δ 7.98 (m, 2H); 7.78 (m, 3H); 7.58 (m, 5H); 7.38 (m, 2H); 5.30 (s, 2H); 4.04 (q, 2H, J=7.0 Hz); 0.89 (t, 3H, J=7.0 Hz). LC MS (CI) shows M+H 471.

Similarly, replacing phthalimide with succinimide, ethyl 6-chloro-2-((2,5-dioxopyrrolidin-1-yl)methyl)-4-phenylquinoline-3-carboxylate was prepared; (704 mg, 83%) as a white powder. $^1$H NMR (CDCl$_3$, 400 MHz) δ 7.9 (d, 1H, J=8.9 Hz); 7.62 (dd, 1H, J=8.9, 2.3 Hz); 7.52 (d, 1H, J=2.3 Hz); 7.51-7.48 (m, 3H); 7.34-7.28 (m, 2H); 5.1 (s, 2H); 4.03 (q, 2H, J=7.4 Hz); 2.9 (bs, 4H); 0.5 (t, 3H, J=7.4 Hz). LC MS (CI) shows M+H 423.

Similarly, replacing phthalimide with tetrazole, ethyl 2-((1H-tetrazol-1-yl)methyl)-6-chloro-4-phenylquinoline-3-carboxylate was prepared; (317 mg, 40%) as a white powder. TLC Rf=0.4 using 1:1 ethyl acetate:hexanes eluent on a silica gel glass backed plate. $^1$H NMR (CDCl$_3$, 400 MHz) δ 8.93 (s, 1H); 7.98 (d, 1H, J=8.9 Hz); 7.72 (dd, 1H, J=8.9, 1.96 Hz); 7.6 (d, 1H, J=1.96 Hz); 7.58-7.48 (m, 3H); 7.36-7.28 (m, 2H); 6.03 (s, 2H); 4.0 (q, 2H, J=7.0 Hz); 0.84 (t, 3H, J=7.0 Hz). LCMS (CI) shows M+H 394.

Similarly, replacing phthalimide with imidazole, ethyl 2-((1H-imidazol-1-yl)methyl)-6-chloro-4-phenylquinoline-3-carboxylate was prepared as a white solid. TLC Rf=0.26 using ethyl acetate as eluent on an alumina plastic backed plate. $^1$H NMR (CDCl$_3$, 400 MHz) δ 8.08 (d, 1H, J=8.9 Hz); 7.72 (bd, 1H, 8.9 Hz); 7.6 (bd, 2H, J=6.3 Hz); 7.5 (bs, 3H); 7.36-7.25 (m, 2H); 7.02 (app bd, 2H, J=12.9 Hz); 5.5 (s, 2H); 3.4 (q, 2H, J=7.4 Hz); 0.74 (t, 3H, J=7.4 Hz). LC MS (CI) shows M+H 392.

Example 9

Preparation of a Compound of Formula (I)

A. Preparation of 2-amino-6-chloro-4-phenylquinoline-3-carbonitrile

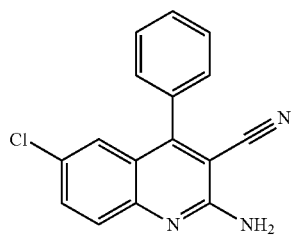 [SMILES: N#Cc1c(N)nc2ccc(Cl)cc2c1-c1ccccc1]

To a yellow solution of 2-amino-5-chlorobenzophenone (2.31 g, 10.0 mmol) in warm (82° C.) dry ethanol (20 ml) was added malononitrile (1.98 g, 30.0 mmol) followed by a solution of sodium ethoxide (9.6 ml of a 3.08 M solution in ethanol, 30.0 mmol). The reaction was heated at reflux for 48 hours, then cooled to room temperature, and the solid filtered off, which was washed with water, ethyl acetate, and dried under reduced pressure to provide 2-amino-6-chloro-4-phenylquinoline-3-carbonitrile as a yellow powder (2.44 g, 87% yield). TLC Rf=0.62 using 1:1 ethyl acetate:hexanes on a silica gel glass backed plate. $^1$H NMR (DMSO-d6; 400 MHz) δ 7.70-7.58 (m, 5H); 7.56-7.5 (m, 2H); 7.22-7.12 (m, 3H). LC MS (CI) shows M+H 280.

Example 10

Preparation of a Compound of Formula (I)

A. Preparation of 1-(6-chloro-2-methyl-4-phenylquinolin-3-yl)ethanol

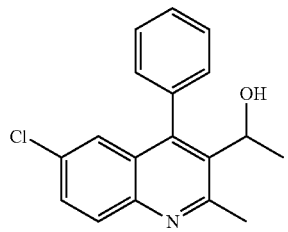 [SMILES: Cc1nc2ccc(Cl)cc2c(-c2ccccc2)c1C(C)O]

To a solution of 1-(6-chloro-2-methyl-4-phenylquinolin-3-yl)ethanone (550 mg, 1.8 mmol) in methanol (10 ml) at room temperature was added portionwise sodium borohydride (315 mg, 8.3 mmol). After the addition the reaction was stirred for 3 hours. Most of the solvent was removed under reduced pressure, the residue diluted with ethyl acetate, and the mixture was poured into a separatory funnel. The organic layer was washed with water (2×), saturated sodium bicarbonate, then brine. The organic phase was separated and solvent removvred under reduced pressure to provide 1-(6-chloro-2-methyl-4-phenylquinolin-3-yl)ethanol (460 mg, 83%) as a white powder. TLC Rf=0.4 using 1:1 ethyl acetate:hexanes as eluent. $^1$H NMR (CDCl$_3$, 400 MHz) δ 7.88 (d, 1H, J=8.9 Hz); 7.54-7.42 (m, 4H); 7.18-7.08 (m, 3H); 5.05 (q, 1H, J=7.0 Hz); 2.95 (s, 3H); 1.0 (d, 3H, J=6.65 Hz). LCMS (CI) shows M+H 297.

Example 11

Preparation of a Compound of Formula (I)

A. Preparation of 2-(2-(4-chlorophenyl)propan-2-yl)-5-(2,4-dimethylquinolin-3-yl)-1,3,4-oxadiazole

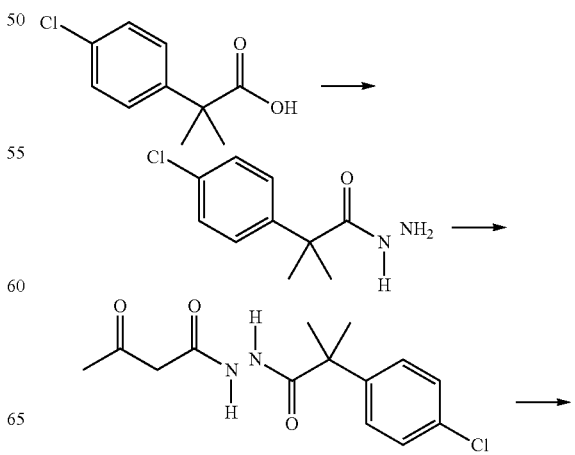

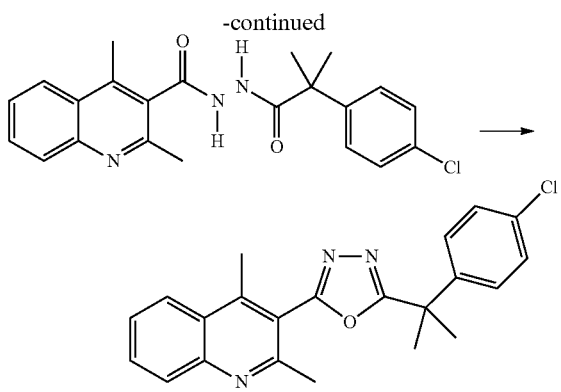

A. Preparation of 2-(4-chlorophenyl)-2-methylpropanehydrazide

To a solution of 2-(4-chlorophenyl)-2-methylpropanoic acid (10.0 g, 50.5 mmol) in dry acetonitrile (100 ml) and dry N,N-dimethylformamide (25 ml) at room temperature was added 1-hydroxybenzotriazole (HOBt, 8.2 g, 61 mmol), followed by ethyl dimethylaminopropylcarbodimide hydrochloride (EDC, 11.65 g, 61 mmol). The mixture was stirred at room temperature for 12 hours, at which time all the starting acid had been consumed as shown by TLC (30% ethyl acetae: hexanes) analysis. The reaction mixture was cooled to 0° C., and slowly added to a solution of hydrazine hydrate at 0° C. (4.8 ml, 100 mmol) in acetonitrile (50 ml). The mixture was stirred at 0° C. for 1 hour, then warmed to room temperature for 3 hours. Solvent was removed under reduced pressure, and the residue diluted with ethyl acetate, which was washed with water (2x), then brine. The organic phase was separated, and solvent removed under reduced pressure to provide 2-(4-chlorophenyl)-2-methylpropanehydrazide (9.64 g, 90%) as a white solid. LCMS (CI) shows M+H 213.

B. Preparation of N'-(2-(4-chlorophenyl)-2-methyl-propanoyl)-3-oxobutanehydrazide 2-(4-chlorophenyl)-2-methylpropanehydrazide (9.0 g, 42.5 mmol) was dissolved in dry tetrahydrofuran (100 ml), and 4-methyleneoxetan-2-one (3.9 ml, 51 mmol) was added dropwise. The reaction mixture was stirred at room temperature for 18 hours, then solvent removed under resuced pressure, and ethyl acetate was added. The solution was passed through a 120 g silica gel column eluting with ethyl acetate, to provide clean N'-(2-(4-chlorophenyl)-2-methylpropanoyl)-3-oxobutanehydrazide (12.2 g, 97%) as a viscous golden oil. TLC Rf=0.47 using 100% ethyl acetate as eluent on a glass backed silica gel plate.

C. Preparation of N'-(2-(4-chlorophenyl)-2-methyl-propanoyl)-2,4-dimethylquinoline-3-carbohydrazide To a solution of N'-(2-(4-chlorophenyl)-2-methylpropanoyl)-3-oxobutanehydrazide (1.77 g, 6.0 mmol) in ethanol (15 ml) was added 2-amino acetophenone (0.61 ml, 5.0 mmol) followed by ytterbium triflate (310 mg, 0.5 mmol). The mixture was heated at 70° C. for 12 hours, cooled to room temperature, and the ethanol was removed under reduced pressure. The crude residue was dissolved in ethyl acetate, poured into a separatory funnel, and washed with water (2x), saturated sodium bicarbonate, and brine. The organic phase was separated, and solvent removed under reduced pressure, to provide a viscous oil, which solidified upon the addition of ethyl ether. The solid was filtered off and washed with diethyl ether, to provide N'-(2-(4-chlorophenyl)-2-methylpropanoyl)-2,4-dimethylquinoline-3-carbohydrazide (1.8 g, 91%) as a light yellow powder. TLC Rf=0.44 using 100% ethyl acetate eluent on a glass backed silica gel plate.

D. Preparation of 2-(2-(4-chlorophenyl)propan-2-yl)-5-(2,4-dimethylquinolin-3-yl)-1,3,4-oxadiazole To a solution of N'-(2-(4-chlorophenyl)-2-methylpropanoyl)-2,4-dimethylquinoline-3-carbohydrazide (592 mg, 1.5 mmol) in dry tetrahydrofuran (5 ml) was added Burgess's reagent (methoxycarbonyl-sulfamoyltriethylammonium inner salt; 714 mg, 3.0 mmol). The mixture was heated at 60° C. for 1 hour, diluted with ethyl acetate, and washed with water, saturated sodium bicarbonate, and then brine. The organic phase was separated, and the solvent removed under reduced pressure, to provide 2-(2-(4-chlorophenyl)propan-2-yl)-5-(2,4-dimethylquinolin-3-yl)-1,3,4-oxadiazole (205 mg, 36%) as a white powder. $^1$H NMR (CDCl$_3$, 400 MHz) δ 8.03 (app t, 2H, J=8.2 Hz); 7.78 (app t, 1H, J=7.0 Hz); 7.58 (app t, 1H, J=7.0 Hz); 7.30 (app q, 4H); 2.56 (s, 3H); 2.51 (s, 3H); 1.90 (s, 6H). LCMS (CI) M+H 378.

Example 12

Preparation of other Compounds of Formula (I)

Similarly, by following the procedures set out in Examples 1 through 11 above, but replacing the starting materials with other appropriately substituted starting materials, the following compounds were prepared:

TABLE 1

| Compound Number | Name of Compound |
|---|---|
| PT-001 | benzyl 2-methyl-4-phenylquinoline-3-carboxylate |
| PT-002 | Tert-butyl 6-chloro-2-methyl-4-phenylquinoline-3-carboxylate |
| PT-003 | 6-chloro-N-(4-fluorobenzyl)-2-methyl-4-phenylquinoline-3-carboxamide |
| PT-004 | 2-amino-6-chloro-4-phenylquinoline-3-carbonitrile |
| PT-005 | 6-chloro-3-[5-(4-chlorobenzyl)-1,3,4-oxadiazol-2-yl]-2-methyl-4-phenylquinoline |
| PT-006 | ethyl 6-chloro-2-(chloromethyl)-4-phenylquinoline-3-carboxylate |
| PT-007 | ethyl 6-chloro-2-[(1,3-dioxo-1,3-dihydro-2H-isoindol-2-yl)methyl]-4-phenylquinoline-3-carboxylate |
| PT-008 | ethyl 6-chloro-2-(1H-imidazol-1-ylmethyl)-4-phenylquinoline-3-carboxylate |
| PT-009 | ethyl 6-chloro-2-[(2,5-dioxopyrrolidin-1-yl)methyl]-4-phenylquinoline-3-carboxylate |
| PT-010 | ethyl 6-chloro-4-phenyl-2-(1H-tetrazol-1-ylmethyl)quinoline-3-carboxylate |
| PT-011 | ethyl 6-chloro-2-[(4-chloro-2-methoxyphenoxy)methyl]-4-phenylquinoline-3-carboxylate |
| PT-012 | cyclopropyl(phenyl)methyl 6-chloro-2-methyl-4-phenylquinoline-3-carboxylate |
| PT-013 | (6-chloro-2-methyl-4-phenylquinolin-3-yl)(piperidin-1-yl)methanone |
| PT-014 | (1S)-1-phenylethyl 6-chloro-2-methyl-4-phenylquinoline-3-carboxylate |
| PT-015 | (1R)-1-phenylethyl 6-chloro-2-methyl-4-phenylquinoline-3-carboxylate |
| PT-016 | cyclopropylmethyl 6-chloro-2-methyl-4-phenylquinoline-3-carboxylate |
| PT-017 | 4-{1-[(6-chloro-2-methyl-4-phenylquinolin-3-yl)carbonyl]piperidin-4-yl}benzamide |
| PT-018 | 4-(1H-pyrazol-1-ylmethyl)benzyl 6-chloro-2-methyl-4-phenylquinoline-3-carboxylate |
| PT-019 | 4-chlorobenzyl 2,4-dimethylquinoline-3-carboxylate |

TABLE 1-continued

| Compound Number | Name of Compound |
|---|---|
| PT-020 | Tert-butyl 6-chloro-4-(2-chlorophenyl)-2-methylquinoline-3-carboxylate |
| PT-021 | ethyl 6-chloro-4-(2-chlorophenyl)-2-methylquinoline-3-carboxylate |
| PT-022 | Tert-butyl 6-chloro-4-(2-fluorophenyl)-2-methylquinoline-3-carboxylate |
| PT-023 | 1-(6-chloro-2-methyl-4-phenylquinolin-3-yl)ethanol |
| PT-024 | ethyl 6-chloro-2-[(dimethylamino)methyl]-4-phenylquinoline-3-carboxylate |
| PT-025 | methyl 2,4-dimethylquinoline-3-carboxylate |
| PT-026 | ethyl 2-(ethoxymethyl)-4-methylquinoline-3-carboxylate |
| PT-027 | 2-bromobenzyl 6-chloro-4-(2-chlorophenyl)-2-methylquinoline-3-carboxylate |
| PT-028 | 2-bromobenzyl 2,4-dimethylquinoline-3-carboxylate |
| PT-029 | ethyl 6-chloro-2-methyl-4-phenylquinoline-3-carboxylate |
| PT-030 | ethyl 6-chloro-4-(2-fluorophenyl)-2-methylquinoline-3-carboxylate |
| PT-031 | 3-{5-[2-(4-chlorophenyl)propan-2-yl]-1,3,4-oxadiazol-2-yl}-2,4-dimethylquinoline |
| PT-032 | 2-bromobenzyl 6-chloro-2,4-dimethylquinoline-3-carboxylate |

Testing

Activity testing was conducted in the Examples below using methods described herein and those well known in the art.

Sodium Current Screening Assays:

The late sodium current (Late INa) and peak sodium current (Peak INa) assays were performed on an automated electrophysiology platform, PatchXpress 7000A (MDS Analytical Technologies, Sunnyvale, Calif.), which uses the whole cell patch clamp technique to measure currents through the cell membrane of up to 16 cells at a time. The assay uses an HEK293 (human embryonic kidney) cell line heterologously expressing the wild-type human cardiac sodium channel, $hNa_v1.5$, purchased from Millipore (Billerica, Mass.). No beta subunits were coexpressed with the Na channel alpha subunit. Cells were maintained with standard tissue culture procedures and stable channel expression was maintained with 400 µg/ml Geneticin in the culture medium. Cells isolated for use on PatchXpress were incubated for 5 minutes in Versene 1X and then for 2 minutes in 0.0125% Trypsin-EDTA (both at 37° C.) to ensure that 80-90% of the cells are single and not part of a cell cluster. Experiments were carried out at 24-27° C.

For both the Late INa and Peak INa assays, series resistance compensation was set to 50% and whole-cell compensation is performed automatically. Currents were low-pass filtered at 10 kHz and digitized at 31.25 kHz. Currents through open sodium channels were automatically recorded and stored in the DataXpress2 database (MDS Analytical Technologies, Sunnyvale, Calif.). Analysis is performed using DataXpress2 analysis software and data are compiled in Excel.

Compound stocks were routinely made in glass vials to 10 mM in dimethyl sulfoxide (DMSO). In some cases, when compounds were not soluble in DMSO, they were made in 100% ethanol. Stocks were sonicated as necessary. The extracellular solution for screening Late INa was composed of: 140 mM NaCl, 4 mM KCl, 1.8 mM $CaCl_2$, 0.75 mM $MgCl_2$, and 5 mM HEPES with pH adjusted to 7.4 using NaOH. The extracellular solution for screening Peak INa was composed of: 20 mM NaCl, 120 mM N-methyl-D glucamine, 4 mM KCl, 1.8 mM $CaCl_2$, 0.75 mM $MgCl_2$, and 5 mM HEPES with pH adjusted to 7.4 using HCl. The intracellular solution used to perfuse the inside of the cells for both the Late INa and Peak INa assays contained: 120 mM CsF, 20 mM CsCl, 5 mM EGTA, 5 mM HEPES and pH adjusted to 7.4 with CsOH. Compounds were diluted in extracellular solution to 10 µM in glass vials and then transferred to glass well plates before robotic addition to the cells. The 0Na extracellular solution used at the end of each experiment for the Late INa and Peak INa assays to measure baseline current contained: 140 mM N-methyl-D-glucamine; 4 mM KCl; 1.8 mM $CaCl_2$; 0.75 mM $MgCl_2$; 5 mM HEPES and pH was adjusted to 7.4 with HCl.

Late INa Screening Assay:

For the Late INa assay, sodium channels were activated every 10 seconds (0.1 Hz) by depolarizing the cell membrane to −20 mV for 250 milliseconds (ms) from a holding potential of −120 mV. In response to a −20 mV voltage step, typical $Na_v1.5$ sodium currents activate rapidly to a peak negative current and then inactivate nearly completely within 3-4 ms.

All compounds were tested to determine their activity in blocking the late sodium current. Late INa current was generated by adding 10 µM Tefluthrin (pyrethroid) to the extracellular solution while recording Na currents.

Peak INa Screening Assay:

Compounds were also evaluated for their effect in several other assays, including their effect on Peak INa. In some cases, the effect on Peak INa was measured using data from the Late INa assay. However, peak currents were often too large to make this possible, requiring a separate assay to evaluate the effect on peak INa. Since the peak INa can be very large, introducing artifacts in the recording, the concentration of $Na^+$ in the bath was reduced to 20 mM and a nonpermeant cation added to compensate for the $Na^+$ that was omitted from the standard extracellular solution (see above). The peak INa assay uses a holding potential of −100 mV and a 20 ms test pulse to 0 mV to activate the channel. As in the Late INa assay, stepping the voltage to 0 mV caused a rapid increase in negative Na current through hNav1.5 that inactivated within a few ms. No late INa activator was added for the peak assay.

For the separate peak INa assay, both tonic (TB) block and use-dependent (UDB) block of peak inward sodium current by 10 µM compound were determined. TB is block of the channel in the resting state, before the channel opens. TB was simulated in this assay by stimulating the channel to open at a low frequency (0.1 Hz). This was done in order to measure the control current amplitude and monitor current rundown, enabling correction for rundown in the calculation of percent block for TB. UDB was measured by stimulating the channel to open at a higher frequency (3 Hz) and was used to determine accumulated block in activated states by compound. Activating the channel at this higher frequency typically also decreased the peak current some even in the absence of compound. Therefore, the assay was designed to measure the use-dependent decrease in peak both in the absence and in the presence of compound, and the calculation of UDB corrects the decrease in current measured in the presence of compound for the decrease in current in the absence of compound.

After establishing the whole cell recording configuration, currents were allowed to stabilize for 6-10 minutes while channels were activated briefly at 0.1 Hz. This was followed by a 2 minute stimulation at 3 Hz and then a 2 minute stimulation at 0.1 Hz before addition of compound. Compound was added 3 times over a period of 2 to 3 minutes and channels were exposed to compound for 8 to 9 minutes before another round of high frequency stimulation at 3 Hz for 2 minutes. As with the late INa assay, 0Na extracellular solution was added two times at the end to establish the baseline current and demonstrate the quality of solution exchange and the recording.

hERG Screening Assay:

Compounds were screened to test their activity in blocking the hERG potassium channel. The hERG channel is heterologously expressed in a CHO (Chinese Hamster Ovary) cell line. Cells were maintained with standard tissue culture procedures and stable channel expression is maintained with 500 µg/ml G418 in the culture medium. Cells were harvested for testing on the PatchXpress automated patch clamp with Accumax (Innovative Cell Technologies, San Diego, Calif.) to isolate single cells.

The following solutions were used for electrophysiological recordings. The external solution contains: 2 mM $CaCl_2$; 2 mM $MgCl_2$; 4 mM KCl; 150 mM NaCl; 10 mM Glucose; 10 mM HEPES (pH 7.4 with 1M NaOH, osmolarity). The internal solution contained: 140 mM KCl, 10 mM $MgCl_2$, 6 mM EGTA, 5 mM HEPES, 5 mM ATP (pH adjusted to 7.25 with KOH).

hERG channels are activated when the voltage is stepped to +20 mV from the −80 mV holding potential. During a 5 second step at +20 mV, the channels activate and then largely inactivate, so the currents are relatively small. Upon returning to −50 mV from +20 mV, hERG currents transiently become much larger as inactivation is rapidly removed and then the channel closes. The first step to −50 mV for 300 ms is used as a baseline for measuring the peak amplitude during the step to −50 mV after channel activation. The peak current at −50 mV was measured both under control conditions and after addition of compound.

All compounds were prepared as 10 mM DMSO stocks in glass vials. Stock solutions were mixed by vigorous vortexing and sonication for about 2 minutes at room temperature. For testing, compounds were diluted in glass vials using an intermediate dilution step in pure DMSO and then further diluted to working concentrations in external solution. Dilutions were prepared no longer than 20 minutes before use.

After achieving the whole-cell configuration, cells were monitored for 90 seconds to assess stability and washed with external solution for 66 seconds. The voltage protocol described above was then applied to the cells every 12 seconds and throughout the whole procedure. Only cells with stable recording parameters and meeting specified health criteria were allowed to enter the compound addition procedure.

External solution containing 0.1% DMSO (vehicle) was applied to the cells first to establish the control peak current amplitude. After allowing the current to stabilize for 3 to 5 minutes, 1 µM and then 10 µM test compounds was applied. Each compound concentration was added 4 times and cells were kept in test solution until the effect of the compound reaches steady state or for a maximum of 12 minutes. After addition of test compound, a positive control (1 µM Cisapride) was added and must block >95% of the current for the experiment to be considered valid. Washout in the external solution compartment was performed until the recovery of the current reaches steady state. Data were analyzed using DataXpress, Clampfit (Molecular Devices, Inc., Sunnyvale) and Origin 7 (Originlab Corp.)

L-type Calcium Channel Activity Well-Plate Assay:

Cell Culture: IMR-32 (human neuroblastoma) cells were obtained from The American Type Culture Collection. The cells were maintained in MEM supplemented with 10% fetal bovine serum, 2 mM of L-glutamine, 100 IU/ml of penicillin, 50 µg/ml of streptomycin, 1% of sodium pyruvate, 1% of sodium bicarbonate and 1% of non-essential amino acid. The cells were cultured at 37° C. in a humidified 5% $CO_2$/95% air incubator. Culture medium was changed every two days and cells were recultivated when they reached 70-80% confluent.

Assay: IMR-32 cells were seeded on a Microtest 96-well Assay Plate (BD FALCON™) at a density of 200,000 cells/well in 200 µl culture medium for overnight. The culture medium was removed, and replaced by 120 µl Ca-4 dye (MDS Analytical Technologies, Sunnyvale, Calif.) in HBSS (1× Hank's Balanced Salt solution plus 20 mM HEPES, pH 7.4) containing 2 mM probenecid. Cells were then incubated for 1 hour at 37° in incubator. Testing compounds were diluted from 5 µM-50 µM in HBSS, and 40 µl were added in cells before assay. L-type calcium channel activities (Max-Min) were measured after addition of 40 µl of 1 µM (−)Bay K 8644 plus 50 mM KCl (final concentration) using FlexStation (Molecular Devices) immediately after addition of testing compounds. The inhibition of L-type calcium channel activity by compounds was then calculated.

Compounds were tested using the described assay methods. Data are shown in Table 2 below. Data are shown for results obtained by testing the listed compounds at a concentration of 10 µM in the late INa and Peak INa assays, and at 1 µM and 10 µM for the hERG and L-type calcium channel assays.

TABLE 2

Assay results

| Compound Number | Late Ina % blk (10 µM test cmpd) | Late Ina % blk (1 µM test cmpd) | hERG Patch Clamp hERG % blk (10 µm test cmpd) | hERG Patch Clamp hERG % blk (1 µm test cmpd) |
|---|---|---|---|---|
| PT-001 | 78.3 | | | |
| PT-002 | 61.1 | | | |
| PT-003 | 26.3 | | | |
| PT-004 | 15.2 | | | |
| PT-005 | 43.6 | | 32.5 | 10.5 |
| PT-006 | 48.8 | | | |
| PT-007 | 24.0 | | | |
| PT-008 | 41.1 | | 94.5 | 43.0 |
| PT-009 | 53.3 | | 65.5 | 24.0 |
| PT-010 | 41.6 | | 66.0 | 18.5 |
| PT-011 | 18.1 | | | |
| PT-012 | 20.5 | | 13.5 | 10.5 |
| PT-013 | 30.2 | | | |
| PT-014 | 36.1 | | | |
| PT-015 | 37.0 | | | |
| PT-016 | 59.0 | | 73.0 | 30.5 |
| PT-017 | 29.4 | | 51.0 | 28.5 |
| PT-018 | 54.5 | | | |
| PT-019 | 70.1 | 22.5 | 62.5 | 10.0 |
| PT-020 | 32.9 | | | |
| PT-021 | 70.2 | | | |
| PT-022 | 46.9 | | | |
| PT-023 | 29.8 | | | |
| PT-024 | 57.8 | | | |
| PT-025 | 26.6 | | | |
| PT-026 | 23.4 | | | |
| PT-027 | 45.3 | | | |
| PT-028 | 82.4 | 39.2 | | |
| PT-029 | 70.2 | | | |
| PT-030 | 55.4 | | | |
| PT-031 | 64.4 | | | |
| PT-032 | 82.4 | | | |

The assay results shown in Table 15 establish that compounds tested showed activity as modulators of late sodium current, for example by inhibiting (or reducing) the late sodium current. (Note that zeroes in the above table may indicate the results were below the level of detection.).

$Na_v1.7$ Screening Assay:

Evidence supports a role for the tetrodotoxin-sensitive $Na_v1.7$ in the pathogenesis of pain. In this assay, whole-cell patch-clamp techniques were used to determine the effects of compounds of Formula (I) on human Nav1.7 (hNav1.7+β1 subunits) channels expressed in HEK293 cells. The Na$_v$1.7 cell line was prepared by stably transfecting HEK293 cells with human Na$_v$1.7 α unit and β1 subunit. HEK293 cells stably expressing huNa$_v$1.7 were analysed by patch clamp techniques and were found to have Na$^+$ currents between −400 and −1800 pA (no currents were recorded in untransfected cells). The Na$^+$ current in these cells was blocked by tetrodotoxin (TTX) with an IC$_{50}$ value of 10-74 nmol/L. Similar results were obtained by use of membrane potential-sensitive dyes.

Stock solutions of compounds of Formula (I) ("test compounds") were prepared in DMSO at a concentration of 40 mmol/L just prior to use. Each test compound was tested in duplicate at 100 µM, then a 1 in 4 serial dilution to yield 8 concentrations for testing. TTX was used as a control inhibitor of Na$_v$1.7 current.

The effect of test compounds to reduce Na$_v$1.7 Na$^+$ current was measured using a fluorescent dye-based membrane potential assay kit (#R8123) from Molecular Devices (California, USA). Briefly, cells were seeded into poly-D-lysine pre-coated black-wall, clear-bottom 96-well Biocoat plates in 100 µl growth media 24 h prior to assay. On the day of the assay the membrane potential dye was prepared and pre-warmed with Hepes-HBSS solution to 37° C. To each well, 100 µl dye was added and incubated at 37° C. for 60 min. Veratridine was added to each well to achieve a final concentration of 50 µmol/L. Test compound was then added to each well in the desired concentration, and fluorescence was recorded. For each test compound data set, an IC$_{50}$ value was calculated based on the assay points generated.

Compounds tested included PT-005 and PT-016. The IC$_{50}$ for each compound as measured in this assay was found to be 37.5 µM (for PT-016) and 0.2 µM (for PT-005). The compounds of Formula (I) were found to block the Nav1.7 current.

In certain embodiments tt is generally desirable that the effects of a compound be specific for the late sodium current and show little or no activity with respect to one or more other ion channels. Thus, in some embodiments, a compound having an activity of reducing late sodium current will also exhibit little or no activity with regard to the peak sodium current. In particular embodiments, a compound having an activity of reducing late sodium current will also exhibit little or no activity with regard to the hERG potassium channel. In some embodiments, a compound having an activity of reducing late sodium current will also exhibit little or no activity with regard to the L-type calcium channel. For example, a given compound may provide a 30% (or greater, e.g. more than 40%, more than 50%, more than 60%, more than 70%, more than 80%) reduction in late sodium current in the assay described herein, and the same compound may exhibit little or no activity for one or more of the peak sodium current, the hERG potassium channel, and the L-type calcium channel. In this regard, a compound having "little" effect will typically show less then a 30% reduction (e.g. less than a 20% reduction, less than a 15% reduction, less than a 10% reduction) in the given activity (e.g. Peak INa, hERG, L-type calcium), when measured using the assay described herein. In this regard, "no" effect means that any activity measured will differ from the control by less than the standard error of the measurement. The assays conducted to measure activities in this regard should be performed as described above, with the compound at a concentration of 10 µM (or at the upper limit of solubility, if less).

In particular embodiments, a compound will exhibit a high selectivity for the late sodium current modulatory activity as compared to the activity in one or more other ion channels. The selectivity of a compound may be determined by determining the percentage reduction in late sodium current due to the compound, as measured by the assay described above. The percentage reduction in one other ion channel activity, such as the hERG potassium channel or L-type calcium channel, due to the compound is determined as described above. The selectivity is determined by taking the ratio of (percentage reduction in late sodium current) to (percentage reduction in one other ion channel activity). The assays conducted to measure activities in this regard should be performed as described above, with the compound at a concentration of 10 µM (or at the upper limit of solubility, if less). In particular embodiments, the selectivity of a compound of the invention will be at least 5:1, e.g. at least 6:1, at least 7:1, at least 8:1, at least 9:1, at least 10:1, at least 12:1, at least 15:1, at least 20:1, or at least 25:1, when comparing the percentage reduction in late sodium current versus percentage reduction of one of the peak sodium current, the hERG potassium channel current, or the L-type calcium channel.

What is claimed is:
1. A compound selected from the group consisting of:
(6-chloro-2-methyl-4-phenylquinolin-3-yl)(piperidin-1-yl)methanone;
4-(1-(6-chloro-2-methyl-4-phenylquinoline-3-carbonyl)piperidin-4-yl)benzamide;
(R)-1-phenylethyl 6-chloro-2-methyl-4-phenylquinoline-3-carboxylate;
(S)-1-phenylethyl 6-chloro-2-methyl-4-phenylquinoline-3-carboxylate;
4-((1H-pyrazol-1-yl)methyl)benzyl 6-chloro-2-methyl-4-phenylquinoline-3-carboxylate;
1-(6-chloro-2-methyl-4-phenylquinolin-3-yl)ethanol;
2-(2-(4-chlorophenyl)propan-2-yl)-5-(2,4-dimethylquinolin-3-yl)-1,3,4-oxadiazole;
benzyl 2-methyl-4-phenylquinoline-3-carboxylate;
tert-butyl 6-chloro-2-methyl-4-phenylquinoline-3-carboxylate;
6-chloro-N-(4-fluorobenzyl)-2-methyl-4-phenylquinoline-3-carboxamide;
6-chloro-3-[5-(4-chlorobenzyl)-1,3,4-oxadiazol-2-yl]-2-methyl-4-phenylquinoline;
cyclopropyl(phenyl)methyl 6-chloro-2-methyl-4-phenylquinoline-3-carboxylate;
(6-chloro-2-methyl-4-phenylquinolin-3-yl)(piperidin-1-yl)methanone;
(1S)-1-phenylethyl 6-chloro-2-methyl-4-phenylquinoline-3-carboxylate;
(1R)-1-phenylethyl 6-chloro-2-methyl-4-phenylquinoline-3-carboxylate;
cyclopropylmethyl 6-chloro-2-methyl-4-phenylquinoline-3-carboxylate;
4-{1-[(6-chloro-2-methyl-4-phenylquinolin-3-yl)carbonyl]piperidin-4-yl}benzamide;
4-(1H-pyrazol-1-ylmethyl)benzyl 6-chloro-2-methyl-4-phenylquinoline-3-carboxylate;
4-chlorobenzyl 2,4-dimethylquinoline-3-carboxylate;
tert-butyl 6-chloro-4-(2-chlorophenyl)-2-methylquinoline-3-carboxylate;
ethyl 6-chloro-4-(2-chlorophenyl)-2-methylquinoline-3-carboxylate;
tert-butyl 6-chloro-4-(2-fluorophenyl)-2-methylquinoline-3-carboxylate;
2-bromobenzyl 6-chloro-4-(2-chlorophenyl)-2-methylquinoline-3-carboxylate;
2-bromobenzyl 2,4-dimethylquinoline-3-carboxylate;

ethyl 6-chloro-2-methyl-4-phenylquinoline-3-carboxylate;
ethyl 6-chloro-4-(2-fluorophenyl)-2-methylquinoline-3-carboxylate; and
3-{5-[2-(4-chlorophenyl)propan-2-yl]-1,3,4-oxadiazol-2-yl}-2,4-dimethylquinoline, or a pharmaceutically acceptable salt thereof.

2. A pharmaceutical composition comprising a pharmaceutically acceptable excipient and a therapeutically effective amount of a compound of claim 1.

* * * * *